United States Patent [19]

Lazarus et al.

[11] Patent Number: 5,719,041
[45] Date of Patent: Feb. 17, 1998

[54] DNA ENCODING ECOTIN HOMOLOGS

[75] Inventors: Robert A. Lazarus, Millbrae; Mark S. Dennis, San Carlos; Jana Seymour Ulmer, San Rafael, all of Calif.

[73] Assignee: Genentech, Inc., South San Francisco, Calif.

[21] Appl. No.: 439,534

[22] Filed: May 11, 1995

Related U.S. Application Data

[62] Division of Ser. No. 319,501, Oct. 4, 1994, which is a continuation of Ser. No. 121,004, Sep. 14, 1993, abandoned.

[51] Int. Cl.$^6$ .......................... C12P 21/02; C12N 15/63; C12N 1/21; C07H 21/04
[52] U.S. Cl. .................. 435/69.2; 435/320.1; 435/252.3; 536/23.7
[58] Field of Search .................... 435/69.1, 320.1, 435/252.3, 252.33, 69.2; 536/23.7, 23.2

[56] References Cited

U.S. PATENT DOCUMENTS 5,370,991 12/1994 Remold-O'Donnell et al. ........... 435/6
5,585,259 12/1996 Lauwereys et al. ...................... 435/226

FOREIGN PATENT DOCUMENTS

WO 94/20535  9/1994  WIPO .

OTHER PUBLICATIONS

Huber et al., "Implications of the Three-Dimensional Structure of $\alpha_1$-Antitrypsinfor Structure and Function of Serpins" *Biochemistry* 28(23):8951–8966 (1989).

McGrath et al., "Macromolecular Chelation as an Improved Mechanism of Protease Inhibition: Structure of Ecotin–Trypsin Complex" *EMBO Journal* 13(7):1502–1507 (1994).

Beckmann et al., "Semisynthesis of Arg 15, Glu 15, Met 15, and Nle 15–Aprotinin Involving Enzymatic Peptide Bond Resynthesis" *J. Protein Chem.* 8(1):101–113 (1989).

Bieth, Joseph G., "In Vivo Significance of Kinetic Constants of Protein Proteinase Inhibitors" *Biochem. Med.* 32:387–397 (1984).

Bigler et al., "Binding of amino acid side chains to preformed cavities: Interaction of serine proteinases with turkey ovomucoid third domains with coded and noncoded P1 residues" *Protein Science* 2:786–799 (1993).

Bone, R.C., "Modulators of Coagulation; A Critical Appraisal of Their Role In Sepsis" *Arch Intern Med* 152:1381–1389 (1992).

Broze, Jr. et al., "Regulation of Coagulation by a Multivalent Kunitz–Type Inhibitor" *Biochemistry* 29(33):7538–7546 (1990).

Carrell et al., "α 1–Antitrypsin and the serpins: variation and countervariation" *TIBS* pp. 20–24 (1985).

Carvalho et al., "Activation of the contact system of plasma proteolysis in the adult respiratory distress syndrome" *J. Lab Clin Med* 112(2):270–277 (1988).

Chung et al., "Purification from *Escherichia coli* of a Periplasmic Protein That Is a Potent Inhibitor of Pancreatic Proteases" *Journal of Biological Chemistry* 258(18):11032–11038 (1983).

Colman, R.W.,"The Role of Plasma Proteases In Septic Shock" *The New England J. of Med.* 320(18):1207–1209 (1989).

Dunwiddie et al., "Site–Directed Analysis of the Functional Domains in the Factor Xa Inhibitor Tick Anticoagulant Peptide: Identification of Two Distinct Regions That Constitute the Enzyme Recognition Sites" *Biochemistry* 31:12126–12131 (1992).

Eisenberg et al., "Importance of Factor Xa in Determining the Procoagulant Activity of Whole–blood Clots" *J. Clin. Invest.* 91:1877–1883 (1993).

Hae Shin et al., "Crystallization and Preliminary X–ray Crystallographic Analysis of the Protease Inhibitor Ecotin" *J. Mol. Biol.* 229:1157–1158 (1993).

Hauptmann et al., "Anticoagulant potential of synthetic and recombinant inhibitors of factor Xa and thrombin in vitro" *Blood Coagulation and Fibrinolysis* 4:577–582 (1993).

Heeb et al., "Inhibition of Activated Protein C by Recombinant α 1–Antitrypsin Variants with Substitution of Arginine or Leucine for Methionine 358" *Journal of Biological Chemistry* 265(4):2365–2369 (1990).

Lauwereys et al., "Ecotin as a Potent Factor Xa Inhibitor" *Thrombosis and Haemostasis* 69(6):783 Abstract 864 (1993).

Lee et al., "Molecular cloning of the Ecotin gene in *Escherichia coli*" *FEBS 09974* 287(1,2):53–56 (1991).

Mahoney et al., "Amino Acid Sequence and Secondary Structural Analysis of the Corn Inhibitor of Trypsin and Activated Hageman Factor" *Journal of Biological Chemistry* 259(13):8412–8416 (1984).

Martinez–Brotons et al., "Plasma Kallikrein–Kinin System in Patients with Uncomplicated Sepsis and Septic Shock–Comparison with Cardiogenic Shock" *Thrombosis and Haemostasis* 58(2):709–713 (1987).

McGrath et al., "Expression of the Protease Inhibitor Ecotin and Its Co–crystallization with Trypsin" *J. Mol. Biol.* 222:139–142 (1991).

McGrath et al., "The Sequence and Reactive Site of Ecotin" *Journal of Biological Chemistry* 266(10):6620–6625 (1991).

Mellott et al., "Enhancement of Recombinant Tissue Plasminogen Activator–induced Reperfusion by Recombinant Tick Anticoagulant Peptide, A Selective Factor Xa Inhibitor, in a Canine Model of Femoral Arterial Thrombosis" *Fibrinolysis* 7:195–202 (1993).

(List continued on next page.)

*Primary Examiner*—Robert A. Wax
*Assistant Examiner*—Kawai Lau
*Attorney, Agent, or Firm*—Jeffrey S. Kubinec

[57] ABSTRACT

A potent serine protease inhibitor capable of inhibiting Factor Xa, Factor XIIa, plasma kallikrein, and human leukocyte elastase is provided. The inhibitor is provided in a pharmaceutical composition for treatment of diseases where inhibition of Factor Xa, Factor XIIa, plasma kallikrein, or HLE is indicated.

9 Claims, 5 Drawing Sheets

OTHER PUBLICATIONS

Patston et al., "Reactivity of α 1–Antitrypsin Mutants against Proteolytic Enzymes of the Kallikrein–Kinin, Complement, and Fibrinolytic System" *Journal of Biological Chemistry* 265(18):10786–10791 (1990).

Pixley et al., "Activation of the Contact System in Lethal Hypotensive Bacteremia in a Baboon Model" *Amer. J. Pathology* 140(4):897–906 (1992).

Pixley et al., "The Contact System Contributes to Hypotension but Not Disseminated Intravascular Coagulation in Lethal Bacteremia" *J Chin Invest* 91:61–68 (1993).

Schapira et al., "Protection by Recombinant α 1–Antitrypsin Ala 357 Arg 358 against Arterial Hypotension Induced by Factor XII Fragment" *J. Clin. Invest.* 80:582–585 (1987).

Schapira et al., "Serine Protease Inhibitors (Serpins)" *Trends Cardiovasc Med* 1(4):146–151 (1991).

Schmaier et al., "Contact Activation and Its Abnormalities" *Hemostasis and Thrombosis; Basic Principles and Clinical Practice*, Colman et al., 2nd edition pp. 18–38 (1987).

Schmeichel et al., "Septic Shock—What Do Physicians Want?" *Biotechnology* 10:264–267 (1992).

Scott et al., "Alpha–1–antitrypsin–Pittsburgh: A Potent Inhibitor of Human Plasma Factor XIa, Kallikrein, and Factor XIIf" *J. Clin. Invest.* 77:631–634 (1986).

Taylor, Jr. et al., "DEGR–Factor Xa Blocks Disseminated Intravascular Coagulation Initiated by *Escherichia coli* Without Preventing Shock or Organ Damage" *Blood* 78(2):364–368 (1991).

Travis et al., "Kinetic Studies on the Interaction of α 1–Proteinase Inhibitor (Pittsburgh) with Trypsin–Like Serine Proteinases" *Biol. Chem. Hoppe–Seyler* 367:853–859 (1986).

Travis, James, Ph.D., "Structure, Function, and Control of Neutrophil Proteinases" *The Amer. Journ. of Med.* 84(6A):37–42 (1988).

Vlasuk et al., "Comparison of the In Vivo Anticoagulant Properties of Standard Heparin and Highly Selective Factor Xa Inhibitors Antistasin and Tick Anticoagulant Peptide (TAP) in a Rabbit Model of Venous Thrombosis" *Thrombosis and Haemostasis* 65(3):257–262 (1991).

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 142 amino acids
( B ) TYPE: amino acid
( D ) TOPOLOGY: linear ( x i ) SEQUENCE DESCRIPTION: SEQ ID NO:1:

```
Ala  Glu  Ser  Val  Gln  Pro  Leu  Glu  Lys  Ile  Ala  Pro  Tyr  Pro  Gln
  1                 5                           10                          15

Ala  Glu  Lys  Gly  Met  Lys  Arg  Gln  Val  Ile  Gln  Leu  Thr  Pro  Gln
                    20                          25                          30

Glu  Asp  Glu  Ser  Thr  Leu  Lys  Val  Glu  Leu  Leu  Ile  Gly  Gln  Thr
                    35                          40                          45
```

| | | | | | | | | | | | | | | |
|---|---|---|---|---|---|---|---|---|---|---|---|---|---|---|
|Leu|Glu|Val|Asp|Cys<br>50|Asn|Leu|His|Arg|Leu<br>55|Gly|Gly|Lys|Leu|Glu<br>60|
|Asn|Lys|Thr|Leu|Glu<br>65|Gly|Trp|Gly|Tyr|Asp<br>70|Tyr|Tyr|Val|Phe|Asp<br>75|
|Lys|Val|Ser|Ser|Pro<br>80|Val|Xaa|Xaa|Xaa|Xaa<br>85|Xaa|Xaa|Pro|Asp|Gly<br>90|
|Lys|Lys|Glu|Lys|Lys<br>95|Phe|Val|Thr|Ala|Tyr<br>100|Leu|Gly|Asp|Ala|Gly<br>105|
|Met|Leu|Arg|Tyr|Asn<br>110|Ser|Lys|Leu|Pro|Ile<br>115|Val|Val|Tyr|Thr|Pro<br>120|
|Asp|Asn|Val|Asp|Val<br>125|Lys|Tyr|Arg|Val|Trp<br>130|Lys|Ala|Glu|Glu|Lys<br>135|
|Ile|Asp|Asn|Ala|Val<br>140|Val|Arg<br>142| | | | | | | | |

( 2 ) INFORMATION FOR SEQ ID NO:2:

( i ) SEQUENCE CHARACTERISTICS:
        ( A ) LENGTH: 142 amino acids
        ( B ) TYPE: amino acid
        ( D ) TOPOLOGY: linear ( x i ) SEQUENCE DESCRIPTION: SEQ ID NO:2:

| | | | | | | | | | | | | | | |
|---|---|---|---|---|---|---|---|---|---|---|---|---|---|---|
|Ala<br>1|Glu|Ser|Val|Gln<br>5|Pro|Leu|Glu|Lys|Ile<br>10|Ala|Pro|Tyr|Pro|Gln<br>15|
|Ala|Glu|Lys|Gly|Met<br>20|Lys|Arg|Gln|Val|Ile<br>25|Gln|Leu|Thr|Pro|Gln<br>30|
|Glu|Asp|Glu|Ser|Thr<br>35|Leu|Lys|Val|Glu|Leu<br>40|Leu|Ile|Gly|Gln|Thr<br>45|
|Leu|Glu|Val|Asp|Cys<br>50|Asn|Leu|His|Arg|Leu<br>55|Gly|Gly|Lys|Leu|Glu<br>60|
|Asn|Lys|Thr|Leu|Glu<br>65|Gly|Trp|Gly|Tyr|Asp<br>70|Tyr|Tyr|Val|Phe|Asp<br>75|
|Lys|Val|Ser|Ser|Pro<br>80|Val|Ser|Xaa|Xaa|Xaa<br>85|Xaa|Cys|Pro|Asp|Gly<br>90|
|Lys|Lys|Glu|Lys|Lys<br>95|Phe|Val|Thr|Ala|Tyr<br>100|Leu|Gly|Asp|Ala|Gly<br>105|
|Met|Leu|Arg|Tyr|Asn<br>110|Ser|Lys|Leu|Pro|Ile<br>115|Val|Val|Tyr|Thr|Pro<br>120|
|Asp|Asn|Val|Asp|Val<br>125|Lys|Tyr|Arg|Val|Trp<br>130|Lys|Ala|Glu|Glu|Lys<br>135|
|Ile|Asp|Asn|Ala|Val<br>140|Val|Arg<br>142| | | | | | | | |

( 2 ) INFORMATION FOR SEQ ID NO:3:

( i ) SEQUENCE CHARACTERISTICS:
        ( A ) LENGTH: 142 amino acids
        ( B ) TYPE: amino acid
        ( D ) TOPOLOGY: linear ( x i ) SEQUENCE DESCRIPTION: SEQ ID NO:3:

| | | | | | | | | | | | | | | |
|---|---|---|---|---|---|---|---|---|---|---|---|---|---|---|
|Ala<br>1|Glu|Ser|Val|Gln<br>5|Pro|Leu|Glu|Lys|Ile<br>10|Ala|Pro|Tyr|Pro|Gln<br>15|
|Ala|Glu|Lys|Gly|Met<br>20|Lys|Arg|Gln|Val|Ile<br>25|Gln|Leu|Thr|Pro|Gln<br>30|
|Glu|Asp|Glu|Ser|Thr<br>35|Leu|Lys|Val|Glu|Leu<br>40|Leu|Ile|Gly|Gln|Thr<br>45|

| | | | | | | | | | | | | | | |
|---|---|---|---|---|---|---|---|---|---|---|---|---|---|---|
| Leu | Glu | Val | Asp | Cys<br>50 | Asn | Leu | His | Arg | Leu<br>55 | Gly | Gly | Lys | Leu | Glu<br>60 |
| Asn | Lys | Thr | Leu | Glu<br>65 | Gly | Trp | Gly | Tyr | Asp<br>70 | Tyr | Tyr | Val | Phe | Asp<br>75 |
| Lys | Val | Ser | Ser | Pro<br>80 | Val | Ser | Thr | Xaa | Xaa<br>85 | Ala | Cys | Pro | Asp | Gly<br>90 |
| Lys | Lys | Glu | Lys | Lys<br>95 | Phe | Val | Thr | Ala | Tyr<br>100 | Leu | Gly | Asp | Ala | Gly<br>105 |
| Met | Leu | Arg | Tyr | Asn<br>110 | Ser | Lys | Leu | Pro | Ile<br>115 | Val | Val | Tyr | Thr | Pro<br>120 |
| Asp | Asn | Val | Asp | Val<br>125 | Lys | Tyr | Arg | Val | Trp<br>130 | Lys | Ala | Glu | Glu | Lys<br>135 |
| Ile | Asp | Asn | Ala | Val<br>140 | Val | Arg<br>142 | | | | | | | | |

( 2 ) INFORMATION FOR SEQ ID NO:4:

( i ) SEQUENCE CHARACTERISTICS:
        ( A ) LENGTH: 142 amino acids
        ( B ) TYPE: amino acid
        ( D ) TOPOLOGY: linear ( x i ) SEQUENCE DESCRIPTION: SEQ ID NO:4:

| | | | | | | | | | | | | | | |
|---|---|---|---|---|---|---|---|---|---|---|---|---|---|---|
| Ala<br>1 | Glu | Ser | Val | Gln<br>5 | Pro | Leu | Glu | Lys | Ile<br>10 | Ala | Pro | Tyr | Pro | Gln<br>15 |
| Ala | Glu | Lys | Gly | Met<br>20 | Lys | Arg | Gln | Val | Ile<br>25 | Gln | Leu | Thr | Pro | Gln<br>30 |
| Glu | Asp | Glu | Ser | Thr<br>35 | Leu | Lys | Val | Glu | Leu<br>40 | Leu | Ile | Gly | Gln | Thr<br>45 |
| Leu | Glu | Val | Asp | Cys<br>50 | Asn | Leu | His | Arg | Leu<br>55 | Gly | Gly | Lys | Leu | Glu<br>60 |
| Asn | Lys | Thr | Leu | Glu<br>65 | Gly | Trp | Gly | Tyr | Asp<br>70 | Tyr | Tyr | Val | Phe | Asp<br>75 |
| Lys | Val | Ser | Ser | Pro<br>80 | Val | Ser | Thr | Xaa | Met<br>85 | Ala | Cys | Pro | Asp | Gly<br>90 |
| Lys | Lys | Glu | Lys | Lys<br>95 | Phe | Val | Thr | Ala | Tyr<br>100 | Leu | Gly | Asp | Ala | Gly<br>105 |
| Met | Leu | Arg | Tyr | Asn<br>110 | Ser | Lys | Leu | Pro | Ile<br>115 | Val | Val | Tyr | Thr | Pro<br>120 |
| Asp | Asn | Val | Asp | Val<br>125 | Lys | Tyr | Arg | Val | Trp<br>130 | Lys | Ala | Glu | Glu | Lys<br>135 |
| Ile | Asp | Asn | Ala | Val<br>140 | Val | Arg<br>142 | | | | | | | | |

( 2 ) INFORMATION FOR SEQ ID NO:5:

( i ) SEQUENCE CHARACTERISTICS:
        ( A ) LENGTH: 142 amino acids
        ( B ) TYPE: amino acid
        ( D ) TOPOLOGY: linear ( x i ) SEQUENCE DESCRIPTION: SEQ ID NO:5:

| | | | | | | | | | | | | | | |
|---|---|---|---|---|---|---|---|---|---|---|---|---|---|---|
| Ala<br>1 | Glu | Ser | Val | Gln<br>5 | Pro | Leu | Glu | Lys | Ile<br>10 | Ala | Pro | Tyr | Pro | Gln<br>15 |
| Ala | Glu | Lys | Gly | Met<br>20 | Lys | Arg | Gln | Val | Ile<br>25 | Gln | Leu | Thr | Pro | Gln<br>30 |
| Glu | Asp | Glu | Ser | Thr<br>35 | Leu | Lys | Val | Glu | Leu<br>40 | Leu | Ile | Gly | Gln | Thr<br>45 |

-continued

```
Leu Glu Val Asp Cys Asn Leu His Arg Leu Gly Gly Lys Leu Glu
                 50              55                       60

Asn Lys Thr Leu Glu Gly Trp Gly Tyr Asp Tyr Tyr Val Phe Asp
                 65              70                       75

Lys Val Ser Ser Pro Val Ser Thr Met Xaa Ala Cys Pro Asp Gly
                 80              85                       90

Lys Lys Glu Lys Lys Phe Val Thr Ala Tyr Leu Gly Asp Ala Gly
                 95             100                      105

Met Leu Arg Tyr Asn Ser Lys Leu Pro Ile Val Val Tyr Thr Pro
                110             115                      120

Asp Asn Val Asp Val Lys Tyr Arg Val Trp Lys Ala Glu Glu Lys
                125             130                      135

Ile Asp Asn Ala Val Val Arg
                140     142
```

(2) INFORMATION FOR SEQ ID NO:6:

(i) SEQUENCE CHARACTERISTICS:
        (A) LENGTH: 38 amino acids
        (B) TYPE: amino acid
        (D) TOPOLOGY: linear (xi) SEQUENCE DESCRIPTION: SEQ ID NO:6:

```
Cys Asn Leu His Arg Leu Gly Gly Lys Leu Glu Asn Lys Thr Leu
 1               5                  10                      15

Glu Gly Trp Gly Tyr Asp Tyr Tyr Val Phe Asp Lys Val Ser Ser
                20                  25                      30

Pro Val Xaa Xaa Xaa Xaa Xaa Cys
                35              38
```

(2) INFORMATION FOR SEQ ID NO:7:

(i) SEQUENCE CHARACTERISTICS:
        (A) LENGTH: 7 amino acids
        (B) TYPE: amino acid
        (D) TOPOLOGY: linear (xi) SEQUENCE DESCRIPTION: SEQ ID NO:7:

```
Pro Asp Gly Lys Lys Glu Lys
 1               5       7
```

(2) INFORMATION FOR SEQ ID NO:8:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:8:

```
Ala Glu Ser Val Gln
 1               5
```

(2) INFORMATION FOR SEQ ID NO:9:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:9:

```
Ala Ala Pro Val
 1           4
```

(2) INFORMATION FOR SEQ ID NO:10:

(i) SEQUENCE CHARACTERISTICS:
(A) LENGTH: 4 amino acids
(B) TYPE: amino acid
(D) TOPOLOGY: linear (xi) SEQUENCE DESCRIPTION: SEQ ID NO:10:

Ala Ala Pro Phe
1               4

(2) INFORMATION FOR SEQ ID NO:11:

(i) SEQUENCE CHARACTERISTICS:
(A) LENGTH: 39 bases
(B) TYPE: nucleic acid
(C) STRANDEDNESS: single
(D) TOPOLOGY: linear (xi) SEQUENCE DESCRIPTION: SEQ ID NO:11:

CTGGACTCTA GAATTATGAA GACCATTCTA CCTGCAGTA 39

(2) INFORMATION FOR SEQ ID NO:12:

(i) SEQUENCE CHARACTERISTICS:
(A) LENGTH: 41 bases
(B) TYPE: nucleic acid
(C) STRANDEDNESS: single
(D) TOPOLOGY: linear (xi) SEQUENCE DESCRIPTION: SEQ ID NO:12:

TCTGAGGATC CAGGCCTTTA GCGAACTACC GCGTTGTCAA T 41

DNA ENCODING ECOTIN HOMOLOGS

This application is a divisional of U.S. patent application Ser. No. 08/319,501 filed Oct. 4, 1994 which is a continuation of U.S. patent application Ser. No. 08/121,004 filed Sep. 14, 1993, now abandoned.

FIELD OF THE INVENTION

This invention relates to ecotin and homologs thereof having the biological activity of ecotin, DNA encoding these homologs, and recombinant materials and methods for producing these homologs. The invention further relates to pharmaceutical compositions containing ecotin and homologs thereof for treatment of diseases where inhibition of Factor Xa, Factor XIIa, plasma kallikrein, or human leukocyte elastase (HLE) is indicated.

BACKGROUND OF THE INVENTION

Ecotin

Ecotin is a previously characterized *E. coli* periplasmic protein known to inhibit the serine proteases; pancreatic trypsin (bovine), pancreatic chymotrypsin (bovine), and elastase (porcine) and has been postulated to play a role in protecting the bacteria from these exogenous proteases found in the mammalian gut (Chung, C. H. et al., *J. Biol. Chem.* 258:11032–11038 [1983]). It does not inhibit any known proteases from *E. coli* (i.e. proteases Do, Re, Mi, Fa, So, La, Ci, Pi, or the esterases "protease I and II"). It is further reported not to inhibit other mammalian serine proteases including; kallikrein, plasmin, and thrombin and non-mammalian proteases; papain(a sulfhydryl protease), pepsin(a carboxyl protease), subtilisin, and thermolysin(a metallo-protease) (Chung, C. H. et al., supra). McGrath et al. (McGrath, M. E. et al.,*J. Biol. Chem.* 266:6620–6625 [1991]), report the cloning and sequencing of this 142 amino acid residue 16,096 Da inhibitor and that the scissile $P_1-P_1'$ bond is Met84–Met85 which lies within a disulfide-bonded loop formed by Cys50 and Cys87. These authors point out that, generally, the $P_1$ residue of a particular serine protease inhibitor needs to be suitably matched with its protease so that favorable binding interactions can be generated between the $P_1$ residue side chain and the substrate binding pocket of the protease. Thus given that trypsin favors the positively charged Lys and Arg at $P_1$, chymotrypsin favors the large hydrophobic Tyr, Phe, Leu, and Met at $P_1$, and elastase favors the small hydrophobic Leu and Val it is surprising that a single inhibitor like ecotin can strongly inhibit all three proteases. The ability of ecotin to inhibit these pancreatic proteases having such widely different $P_1$ binding pockets has been attributed to the $P_1$ Met residue which is apparently well tolerated by all three proteases while still generating significant binding energy. Other serine protease inhibitors having Met at $P_1$ that show this pan inhibition of the three pancreatic proteases include certain Kazal-type inhibitors and $\alpha_1$-proteinase inhibitor (sometimes referred to as $\alpha_1$-antitrypsin).

Serpins(serine protease inhibitors) such as $\alpha_1$-proteinase inhibitor have been well charcterized for their ability to inhibit various proteases because of their therapeutic potential to control proteolysis in thrombosis, shock, and inflammation (Schapira, M. et al., *Trends Cardiovasc. Med.,* 4:146–151 [1991]; Patston, P. A. et al., *J. Biol. Chem.* 265:10786–10791 [1990]) and because spontaneous mutations to the $P_1$ residue (Met$^{358}$-Arg$^{358}$; $\alpha_1$-proteinase inhibitor-Pittsburgh) dramatically alter the protease inhibitor specificity (Scott, C. F. et al., *J. Clin. Invest.* 77:631–634 [1986]). $\alpha_1$-Proteinase inhibitor, having a Met residue at $P_1$, is known to be a poor inhibitor of Factor Xa (Travis, J. et al., *Biol. Chem. Hoppe-Seyler* 367:853–859 [1986]; see e.g. table page 857) as well as Factor XIIf (Scott, C. F. et al., supra; see Table I, page 632) and kallikrein (Scott, C. F. et al., supra; Schapira, M. et al., supra see Table 4, page 148). Thus from statements made in the literature and reasoning by analogy with other protease inhibitors having a $P_1$-Met, one would not predict that ecotin would be a good inhibitor of FXa, FXIIa or kallikrein.

Factor Xa

Factor Xa (FXa) is a vitamin K-dependent glycosylated serine protease that plays a fundamental role in the coagulation cascade (see FIG. 1) and in maintaining hemostasis (Davie, E. W. et al., *Biochemistry* 30:10363–10370 [1991]), (Mann, K. G. et al., *Semin. Hematol.* 29:213–226 [1992]). It is produced from its zymogen Factor X upon activation of either the intrinsic or extrinsic pathways of coagulation and, in the presence of Factor Va, Ca$^{2+}$ and a suitable phospholipid surface, forms the prothrombinase complex. This complex generates thrombin which ultimately results in the formation of a stable fibrin clot. Since FXa is common to both coagulation pathways, anticoagulants that target inhibition of FXa may prevent fibrin-rich thrombus formation and have utility in the treatment of thrombotic diseases.

Factor Xa is regulated by at least two different plasma protease inhibitors in vivo antithrombin III and tissue factor pathway inhibitor. Antithrombin III (ATIII) is a serpin that, in the presence of heparin or other glycosaminoglycans, gives rise to rapid and irreversible inhibition of FXa, thrombin, and other plasma proteases (Björk, I. & Danielsson, Å. in *Proteinase Inhibitors* (Barrett, A. J. & Salvesen, G., Ed.) pp 489–513, Elsevier, Amsterdam [1986]). ATIII contains Arg-Ser at the $P_1-P_1'$ residues. The mechanism of heparin mediated ATIII inhibition is thought to involve either a conformational change in ATIII or the formation of a ternary complex (Björk, I. and Danielsson, Å, supra). Tissue factor pathway inhibitor (TFPI) is a protein containing three tandem Kunitz domains that is a slow tight-binding inhibitor of FXa. TFPI also inhibits the tissue factor•Factor VIIa (TF•FVIIa) complex in a FXa-dependent manner (Broze Jr., G. J. et al.,*Biochemistry* 29:7539–7546 [1990]). Based on in vitro properties of TFPI, it is thought to regulate the tissue factor induced (extrinsic) coagulation pathway by a feedback mechanism (Broze Jr., G. J. *Semin. Hematol.* 29:159–169 [1992]).

Antistasin and tick anticoagulant peptide are two potent inhibitors of FXa from exogenous sources that have recently been described. Antistasin is a potent 119-residue protein inhibitor of FXa found in the salivary glands of the Mexican leech *H. officinalis* (Tuszynski, G. P. et al., *J. Biol. Chem.* 262:9718–9723 [1987]). It is a reversible slow tight-binding inhibitor with an estimated dissociation constant between 0.31 and 0.62 nM (Dunwiddie, C. T. et al., *J. Biol. Chem.* 264:16694–16699 [1989]). Tick anticoagulant peptide (TAP) is a 60-residue protein derived from the salivary glands of the tick *O. moubata* that also reversibly and potently inhibits FXa (Waxman, L. et al., *Science* 248:593–596 [1990]) with a dissociation constants of between 0.18 and 0.59 nM (Jordan, S. P. et al.,*Biochemistry* 29:11095–11100 [1990]). Both antistasin and TAP prevent venous thrombosis in a rabbit model (Vlasuk, G. P. et al.,*Thrombosis and Hemostasis* 65:257–262 [1991]). Infusion of DEGR-FXa, a specific FXa inhibitor in which the active site of FXa is blocked, in a baboon model of sepsis led to the prevention of disseminated intravascular coagulation (DIC); however DEGR-FXa did not prevent shock or organ damage (Taylor Jr., F. B. et al., *Blood* 78:364–368 [1991]).

Factor XII

Factor XII (FXII) is a glycoprotein having a single polypeptide chain (596 amino acids) with a molecular weight of 80,000 Da and is present in normal plasma at a concentration of ca. 30 µg/ml (400 nM). It is a serine protease zymogen which requires cleavage at the 353–354 peptide bond to become activated to Factor XIIa (FXIIa). Factor XII is the first enzyme in the intrinsic pathway (see FIG. 1) of blood coagulation and can be autoactivated by the exposure of human plasma to negatively charged surfaces such as glass, connective tissue or collagen, endotoxin, and a wide variety of other endogenous or exogenous components. In the presence of high molecular weight kininogen, Factor XIIa can activate prekallikrein to kallikrein and Factor XI to Factor XIa; the kallikrein formed can activate more Factor XII to FXIIa (see FIG. 1). Factor XIa then activates Factor IXa, which in the presence of Factor VIIIa activates Factor X to Factor Xa. Factor Xa activates prothrombin to thrombin which cleaves fibrinogen to fibrin and ultimately results in the formation of a stable fibrin clot. Factor XIIa has also been implicated in the activation of Factor VII, which in the presence of tissue factor can also activate Factor X to Factor Xa. Factor XIIa can also activate the complement pathway and activate neutrophils through the generation of chemotactic peptides.

Further proteolytic cleavage of Factor XIIa can occur removing a portion of the amino terminus resulting in a 28,000 Da protease, Factor XIIf ($\beta$-FXIIa). Both Factor XIIa and Factor XIIf are capable of activating prekallikrein to kallikrein; however, Factor XIIf is no longer able to bind negatively charged surfaces and is at least 100 times less potent in the activation of Factor XI.

C1 inhibitor, a naturally occuring human protein inhibitor belonging to the serpin family of protease inhibitors, binds irreversibly to Factor XIIa and is the primary physiological inhibitor accounting for >90% of the inhibitory activity of plasma. C1 inhibitor contains residues Ala-Arg at the $P_2$—$P_1$ positions (compare with $\alpha_1$-proteinase inhibitor-Pittsburgh below). Antithrombin III, can also inhibit Factor XIIa, however the rate of inhibition is much slower than with thrombin or Factor Xa.

A number of exogenous protein inhibitors of Factor XIIa have been identified. Squash contains small 29 amino acid inhibitors, designated CMTI, that are inhibitors of Factor XIIa; the $K_i$ for CMTI-III was 3 nM (Wynn, R. & Laskowski Jr., M., *Biochem. Biophys Res. Commun.* 166:1406–1410 [1990]). This inhibitor (also known as Pumpkin seed Hageman Factor inhibitor ) did not inhibit plasma kallikrein, pancreatic kallikrein, or thrombin, but weakly inhibited plasmin and Factor Xa (Hojima, Y. et al., *Biochemistry* 21:3741–3746 [1982]). The $P_1$ residues for the CMTI family of inhibitors are either Arg or Lys. In addition, corn contains a 112 residue inhibitor known only to inhibit trypsin and Factor XIIa; the $P_1$ residue is Arg (Mahoney, W. C. et al., *J. Biol. Chem.* 259:8412–8416 [1984]).

A monoclonal antibody (C6B7) to Factor XII has been shown to prevent irreversible hypotension observed in a baboon model of *E. coli* induced septicemia and prolong the survival time compared to an untreated group. The activation of the contact pathway was manifested by a decrease in HMWK and an increase in $\alpha$2-macroglobulin-kallikrein complexes. However, disseminated intravascular coagulation (DIC) manifested by decreased platelet, fibrinogen and Factor V levels, was not prevented (Pixley, R. A. et al., *J. Clin. Invest.* 91:61–68 [1993]).

A mutant form of $\alpha_1$-proteinase inhibitor ($\alpha_1$-proteinase inhibitor-Pittsburgh) that contains an Arg in the $P_1$ position and an Ala in the $P_2$ position has been shown to be a more potent inhibitor of Factor XIIf and kallikrein compared to C1 inhibitor, the most potent known natural inhibitor of these proteases (Schapira, M. et al., *J. Clin. Invest* 80:582–585 [1987]; Patston, P. A. et al., supra). Rats treated with this mutant were partially protected from the hypotension resulting from injection of Factor XIIf.

Kallikrein

Prekallikrein is a glycoprotein comprised of a single polypeptide chain with a molecular weight of 80,000 Da and is present in normal plasma at a concentration of about 50 µg/ml (600 nM). In blood, 75% of prekallikrein circulates bound to HMWK. Prekallikrein is a serine protease zymogen that can be activated by Factor XIIa to form kallikrein. Kallikrein is composed of 2 polypeptide chains of 43,000 and 33,000–36,000 Da which are linked through disulfide bonds. The light chain of kallikrein contains the enzymatic domain while the heavy chain appears to be required for surface dependent activation of coagulation.

Kallikrein cleaves HMWK to form bradykinin (a potent vasodilator and endothelial cell activator), can activate prourokinase and plasminogen (fibrinolytic), and feeds back for reciprocal activation of surface bound FXII to FXIIa (see FIG. 1). In addition, kallikrein can stimulate neutrophils causing the release of elastase. Both Factor XIIa and kallikrein can lead to plasmin generation causing fibrinolysis.

The major physiological inhibitor of kallikrein is C1 inhibitor which causes irreversible inhibition. In a purified system HMWK has been shown to protect kallikrein from inhibition by C1 inhibitor although both proteins bind to kallikrein at different sites. $\alpha$2-macroglobulin is another major inhibitor of kallikrein. Antithrombin-III can also inhibit kallikrein, but slowly even in the presence of heparin. $\alpha$2-antiplasmin and $\alpha_1$-proteinase inhibitor are poor inhibitors of kallikrein.

Exogenous protein inhibitors of kallikrein include basic pancreatic trypsin inhibitor (BPTI, aprotinin) which reversibly inhibits plasma kallikrein as well as plasmin and a number of other serine proteases; the $P_1$ residue of BPTI is a Lys. BPTI has been used to treat patients with acute pancreatitis (Fritz, H. & Wunderer, G., *Arzneim.-Forsch. Drug Res.* 33:479–494 [1983]). The use of aprotinin and the possible involvement of the contact pathway (see below) has also been described for the reduction of bleeding from postoperative surgery (Royston, D. *Blood Coag. Fibrinol.* 1:55–69 [1990]) and in cardiopulmonary bypass surgery (Fuhrer, G. et al., *Blood Coag. Fibrinol.* 3:99–104 [1992]). Similarly, soybean trypsin inhibitor has been shown to inhibit bradykinin formation and the initial hypotension induced by endotoxin in rats (Katori, M., et al., *Br. J. Pharmacol.* 98:1383–1391 [1989]).

Human Leukocyte Elastase

Human leukocyte elastase (HLE) is an abundant serine protease present in the azurophilic granules of neutrophils (Bieth, J. G. in *Regulation of Matrix Accumulation* (Mecham, R. P., Ed.) pp 217–320, Academic Press, Orlando [1986]; Stein, R. L. et al., *Annu. Rep. Med. Chem.* 20:237–246 [1985]). It has been implicated in the proteolytic destruction of connective tissue proteins and the pathogenesis of diseases such as emphysema, chronic bronchitis, cystic fibrosis, rheumatoid arthritis, ARDS, and sepsis (Gadek, J. E. & Pacht, E. R., *Lung Suppl.*:552–564 [1990]; Janoff, A. *Annu. Rev. Med.* 36:207–216 [1985]; Janoff, A. *Am. Rev. Respir. Dis.* 132:417–433 [1985]). The regulation of HLE is mediated by a number of naturally occurring protease inhibitors (Travis, J. *Am. J. Med.* 84Suppl. 6A:37–42 [1988]) including $\alpha_1$-proteinase inhibitor (Heidtmann, H. & Travis, J., in *Proteinase inhibitors* (Barrett, A. J. and Salvesen, G., Eds.) pp 441–456, Elsevier, Amsterdam [1986]), secretory leukocyte proteinase inhibitor or mucous proteinase inhibitor, a 107 residue protein found in various mucosal fluids (Thompson, R. C. & Ohlsson, K., *Proc. Natl. Acad. Sci. USA* 83:6692–6696 [1986]), and elafin, a 57 residue protein isolated from psoriatic skin (Wiedow, O. et al.,*J. Biol. Chem.* 265:14791–14795 [1990]). During an inflammatory response, HLE is released from neutrophils and its inhibitors may become oxidatively inactivated leading to increased pathogenic HLE mediated proteolysis. Thus, alternative HLE inhibitors may be useful in controlling diseases associated with pathogenic levels of this enzyme (Travis, J., *Am. J. Med.*, supra; Zimmerman, M. & Powers, J. C. in *Elastin and Elastases* (Ladislas, R., Ed.) pp 109–123, CRC Press, Boca Raton [1989]).

HLE has also been implicated in the regulation of fibrinolysis involving activation or degradation of key proteins of the fibrinolytic pathway (Machovich, R & Owen, W. G., *Blood Coag. Fibrinol.* 1:79–90 [1990]). In addition HLE has been shown to cleave TFPI between the first and second Kunitz domains resulting in a marked decrease in the ability of this protein to inhibit tissue factor·Factor VIIa or Factor Xa (Higuchi D. A. et al., *Blood* 79:1712–1719 [1992]). HLE may also inactivate Factor VII by limited proteolysis (Anderssen, T. et al. *Thromb. Haemostasis* 70:414–417 [1993]). HLE can also inactivate serpins such as antithrombin III, heparin cofactor II, and C1 inhibitor. Therefore inhibition of HLE may play a key role in regulating coagulation, contact activation, and complement pathways (see FIG. 1).

Contact Activation Pathways in Disease

Contact activation is a surface mediated pathway responsible in part for the regulation of inflammation and coagulation. The proteins involved in this pathway include Factor XII (Hageman Factor), prekallikrein (Fletcher Factor), high molecular weight kininogen (HMWK), and C1 inhibitor (Schmaier, A. H. et al., in *Hemostasis and Thrombosis: Basic Principles and Clinical Practice* (Colman, R. W., Hirsh, J., Marder, V., & Salzman, E. W., Eds.) pp 18–38, J. B. Lippincott Co., Philadelphia [1987]). The involvement of this plasma protease system has been suggested to play a significant role in a variety of clinical manifestations including septic shock, adult respiratory distress syndrome (ARDS), disseminated intravascular coagulation (DIC) and various other disease states (Coleman R. W. N. *Engl. J. Med* 320:1207–1209 [1989]); Bone, R. C. *Arch. Intern. Med.* 152:1381–1389 [1992]).

Septic shock

Septic shock is the most common cause of death of humans in intensive care units in the United States (Parillo, J. E. et al., *Ann. Int. Med.* 113:227–242 [1990]; Schmeichel C. J. & McCormick D., *BioTechnol.* 10:264–267 [1992]). It is usually initiated by a local nidus of infection that invades the blood stream. Incidences of sepsis and shock can arise from infections with either gram negative, gram positive bacterial or fungal microorganisms. All these organisms seem to induce a common pattern of cardiovascular dysfunction. In recent years aggressive fluid infusion therapy has been accepted as a primary means of treatment for septic shock. Adequate repletion of fluid is associated with an elevated cardiac output and low vascular resistance. Despite treatment, septic shock results in a severe decrease in systemic vascular resistance and generalized blood flow maldistribution. Aggressive therapy reverses shock and death in about 50% of the cases. Unresponsive hypotension resulting from a very low vascular resistance cannot be corrected by fluid infusion. Among those subjects that die from septic shock, approximately 75% die from persistent hypotension and the remainder due to multiple organ system failure (see FIG. 1).

The increase in cardiac output and vasodilation in septic shock is attributed to the action of inflammatory mediators. While the actual events leading to septic shock, DIC and hypotension have not been established, the known interactions among various components of the many physiological systems suggest that activation of the contact pathway may lead to a state of septic shock, multiorgan failure, and death (Bone, R. C., supra) as illustrated in FIG. 1. The contact system of intrinsic coagulation and the complement system are excessively activated in sepsis and septic shock, especially in cases of fatal septic shock. The contact system can participate in the generation of many vasoactive mediators such as bradykinin, FXIIa, FXIIf and C5a, which are thought to play a role in the pathogenesis of fatal shock. Bradykinin, FXIIa, and XIIf are potent inducers of hypotension while C5a is an inducer of vasodilation and vasopermeability. The levels of FXII, prekallikrein, and high molecular weight kininogen are decreased significantly during non-fatal shock, but are most severely depressed during fatal septic shock to approximately 30%, 57% and 27% of normal values respectively. These changes are noted regardless of whether the septic state is caused by gram positive or gram negative bacteria. The contact activation pathway is also involved in both fibrin deposition and lysis, as well as triggering neutrophil activation, activation of complement and modulation of blood pressure.

Decreased levels of prekallikrein are observed in hepatic disease, DIC, chronic renal failure and nephritic syndrome. In septic shock, components of the kallikrein-kinin system are depleted suggesting activation of this system. This is not the case in cardiogenic shock suggesting that the kallikrein-kinin system is a key player in septic shock (Martinez-Brotons F. et al., *Thromb. Haemostas.* 58:709–713 [1987])

ARDS

ARDS is a complex pulmonary disorder affecting 150,000 people in the U.S. yearly with a 50% mortality rate. Leukocytes, platelets and the proteolytic pathways of coagulation and complement mediate ARDS. ARDS involves activation of the contact activation pathway and depletion of C1 inhibitor. Sepsis induced ARDS results in more severe DIC and fibrinolysis, more fibrin degradation products and reduced ATIII levels compared to trauma induced ARDS (Carvalho, A. C. et al., *J. Lab. Clin. Med.* 112:270–277 [1988]).

Disseminated Intravascular Coagulation

Disseminated intravascular coagulation (DIC) is a disorder that occurs in response to tissue injury and invading microorganisms characterized by widespread deposition of fibrin and depleted levels of fibrinogen (Muller-Berghaus, G. *Semin. Thromb. Hemostasis* 15:58–87 [1989]). There are prolonged prothrombin and activated partial thromboplastin times. DIC has been observed in the clinical settings of a wide variety of diseases (Fruchtman, S. M. & Rand, J. H. in *Thrombosis in Cardiovascular Disorders* (Fuster, V. & Verstraete M. eds.) pp 501–513 W. B. Saunders, Philadelphia [1992]).

Hypotension, DIC, and neutrophil activation are all triggered by the interaction of Factor XIIa, plasma kininogens and kallikrein. Deficiency of any of these 3 proteins does not give rise to hemostatic disorders due to redundancy in the system due to platelets, other coagulation factors, and endothelial cells.

A large number of therapeutic approaches to septic shock and related disorders have been identified including various cytokine antagonists, Mabs (to endotoxin, tissue factor, tumor necrosis factor (TNF), neutrophils, etc.), kinin antagonists, bacteriocidal permeability increasing protein, PAF antagonists, C1 inhibitor, DEGR-FXa, activated protein C, and many other approaches. It is possible, due to the complicated nature of the disease, that an approach that involves multiple agents or agents that effect multiple pathways may be successful in the treatment of septic shock (Schmeichel C. J. & McCormick D., supra).

Accordingly, it is an object of this invention to provide potent serine protease inhibitors that reversibly inhibit proteases of the coagulation, contact activation, fibrinolysis, inflammation, complement activation, and hypotensive pathways for the treatment of diseases that are affected by these pathways. It is further an object of this invention to provide potent inhibitors capable of inhibiting Factor Xa, Factor XIIa, kallikrein, and HLE. Additionally, it is an object to provide synthetic methods for producing these inhibitors for therapeutic intervention. These and other objects will be apparent from consideration of this application as a whole.

SUMMARY OF THE INVENTION

By means of the present invention the objectives described above have been realized, and there is accordingly provided herein a composition of matter capable of inhibiting a serine protease selected from Factor Xa, Factor XIIa, plasma kallikrein, and human leukocyte elastase (HLE), comprising a purified polypeptide selected from ecotin analogs, ecotin homologs and a purified amino acid sequence selected from Formula I–V:

| | |
|---|---|
| $R^1$—$P^3$—$P^2$—$P^1$—$P^{1'}$—$P^{2'}$—$P^{3'}$—$R^2$ (SEQ ID NO:1), | I |
| $R^1$—Ser—$P^2$—$P^1$—$P^{1'}$—$P^{2'}$—Cys—$R^2$ (SEQ ID NO:2), | II |
| $R^1$—Ser—Thr—$P^1$—$P^{1'}$—Ala—Cys—$R^2$ (SEQ ID NO:3), | III |
| $R^1$—Ser—Thr—$P^1$—Met—Ala—Cys—$R^2$ (SEQ ID NO:4), | IV |
| $R^1$—Ser—Thr—Met—$P^{1'}$—Ala—Cys—$R^2$ (SEQ ID NO:5), and | V | where $P^3$, $P^2$, $P^1$, $P^{1'}$, $P^{2'}$ and $P^{3'}$ are the same or different and are selected from the naturally occuring amino acid residues, provided $P^3$, $P^2$, $P^1$, $P^{1'}$, $P^{2'}$ and $P^{3'}$ are not simultaneously Ser, Thr, Met, Met, Ala, and Cys respectively, $R^1$ represents amino acid residues 1–81 of ecotin or conservative amino acid substitutions or deletions thereof, $R^2$ represents amino acid residues 88–142 of ecotin or conservative amino acid substitutions or deletions thereof, and pharmaceutically acceptable salts thereof. A prefered composition of matter is represented by Formula IV where $P^1$ is a naturally occuring amino acid residue other than Met, $R^1$ represents amino acid residues 1–81 of ecotin and $R^2$ represents amino acid residues 88–142 of ecotin. More preferably, in one embodiment of the invention $P^1$ of Formula IV is selected from Arg, Lys, Ala, Asp, and Glu. When inhibition of FXII, Kallikrein, or FXa is desired, the most preferred $P^1$ is Arg or Lys. When inhibition of HLE is desired, the most preferred $P^1$ is Met, Val, Leu or Ala.

An alternative prefered composition of matter is represented by Formula V where $P^1$ is a naturally occuring amino acid residue other than Met, $R^1$ represents amino acid residues 1–81 of ecotin and $R^2$ represents amino acid residues 88–142 of ecotin.

In still another alternative embodiment of the invention there is provided a purified amino acid sequence represented by Formula VI $H_2$N-Cys-Asn-Leu-His-Arg-Leu-Gly-Gly-Lys-Leu-Glu-Asn-Lys-Thr-Leu-Glu-Gly-Trp-Gly-Tyr-Asp-Tyr-Tyr-Val-Phe-Asp-Lys-Val-Ser-Ser-Pro-Val-$P^3$-$P^2$-$P^1$-$P^{1'}$-$P^{2'}$-Cys-OH (SEQ ID NO:6)VI or conservative amino acid substitutions thereof, where, $P^3$, $P^2$, $P^1$, $P^{1'}$ and $P^{2'}$ are the same or different and are selected from the naturally occuring amino acid residues and pharmaceutically acceptable salts thereof. Preferably, $P^3$ will be Ser, $P^2$ will be Thr, $P^1$ will be Lys, Arg, Met, Val, Leu, or Ala, $P^{1'}$ will be Met, and $P^{2'}$ will be Ala.

The composition of matter of this invention preferably has a $K_i$ with Factor Xa of less than 1 nM, and most preferably less than 100 pM.

The composition of matter of this invention preferably has a $K_i$ with Factor XIIa of less than 1 nM, and most preferably less than 100 pM.

The composition of matter of this invention preferably has a $K_i$ with plasma kallikrein of less than 1 nM, and most preferably less than 100 pM.

The composition of matter of this invention preferably has a $K_i$ with HLE of less than 1 nM, and most preferably less than 100 pM.

In a further embodiment, the present invention encompasses a composition of matter comprising isolated nucleic acid, preferably DNA, encoding the protein component of a composition of matter comprising a polypeptide selected from ecotin analogs, ecotin homologs and a purified amino acid sequence represented by Formula I–VI. The invention further comprises an expression control sequence operably linked to the DNA molecule, an expression vector, preferably a plasmid, comprising the DNA molecule, where the control sequence is recognized by a host cell transformed with the vector, and a host cell transformed with the vector.

Prefered expression vectors of the present invention may be selected from; pBR322, phGH1, pBO475, pRIT5, pRIT2T, pKK233-2, pDR540, and pPL-lambda, with the most preferred vector being phGH1.

Prefered host cells containing the expression vector of the present invention may be selected from *E. coli* K12 strain 294 (ATCC No. 31446), *E. coli* strain JM101, *E. coli* B, *E. coli* X1776 (ATCC No. 31537), *E. coli* c600, *E. coli* W3110 (F-, gamma-, prototrophic, ATCC No. 27325), *Bacillus subtilis, Salmonella typhimurium, Serratia marcesans*, and Pseudomonas species, with the most preferred host cell being *E. coli* W3110 (ATCC No. 27325), or a derivative thereof such as the protease deficient strain 27C7.

The composition of the present invention may be made by a process which includes the steps of isolating or synthesizing nucleic acid sequences encoding any of the amino acid sequences described above, ligating the nucleic acid sequence into a suitable expression vector capable of expressing the nucleic acid sequence in a suitable host, transforming the host with the expression vector into which the nucleic acid sequence has been ligated, culturing the host under conditions suitable for expression of the nucleic acid sequence, whereby the protein encoded by the selected nucleic acid sequence is expressed by the host. In this process, the ligating step may further contemplate ligating the nucleic acid into a suitable expression vector such that the nucleic acid is operably linked to a suitable secretory signal, whereby the amino acid sequence is secreted by the host. The secretory signal may be selected from the group consisting of the leader sequence of ecotin, stII, lamB, herpes gD, lpp, alkaline phosphatase, invertase, and alpha factor, is preferably ecotin or stII, and is most preferably the leader sequence of ecotin.

The present invention further extends to therapeutic applications for the compositions described herein and to ecotin per se. Thus the invention includes a pharmaceutical composition comprising a pharmaceutically acceptable excipient and ecotin, analogs of ecotin, homologs of ecotin and a purified amino acid sequence represented by Formula I–VI.

Those applications include, for example, a method for inhibiting thrombus formation in a mammal comprising administering a pharmaceutically effective amount of the pharmaceutical composition to the mammal. The pharmaceutically effective amount may be between about 0.001 nM and 1.0 mM, is preferably between about 0.1 nM and 100 µM, and is most preferably between about 1.0 nM and 50 µM. Additionally, the pharmaceutical composition may be administered prior to, following, or simultaneously with administration of a fibrinolytic or thrombolytic agent such as tissue plasminogen activator, streptokinase, urokinase, prourokinase, and modifications thereof. Alternatively the pharmaceutical composition may be administered in combination with an anticoagulant.

Additionally, other applications include, for example, a method of treating a mammal for which inhibiting Factor Xa, Factor XIIa, plasma kallikrein, or HLE is indicated comprising administering a pharmaceutically effective amount of the pharmaceutical composition to the mammal. Such indications include; inflammation, septic shock, hypotension, ARDS, DIC, cardiopulmonary bypass surgery, and bleeding from postoperative surgery.

BRIEF DESCRIPTION OF THE FIGURES

FIG. 4A, measurement of the association rate constant of ecotin with FXa. The curve results from nonlinear regression analysis of the data to equation 4. FIGS. 4A and 4B, measurement of the dissociation rate constant of ecotin from FXa in the presence of HLE (●) and in the absence of HLE (▲). The curves result from nonlinear regression analysis of the data to equation 6, where the measured velocity is proportional to free [FXa].

DETAILED DESCRIPTION OF THE INVENTION

Figure 1:
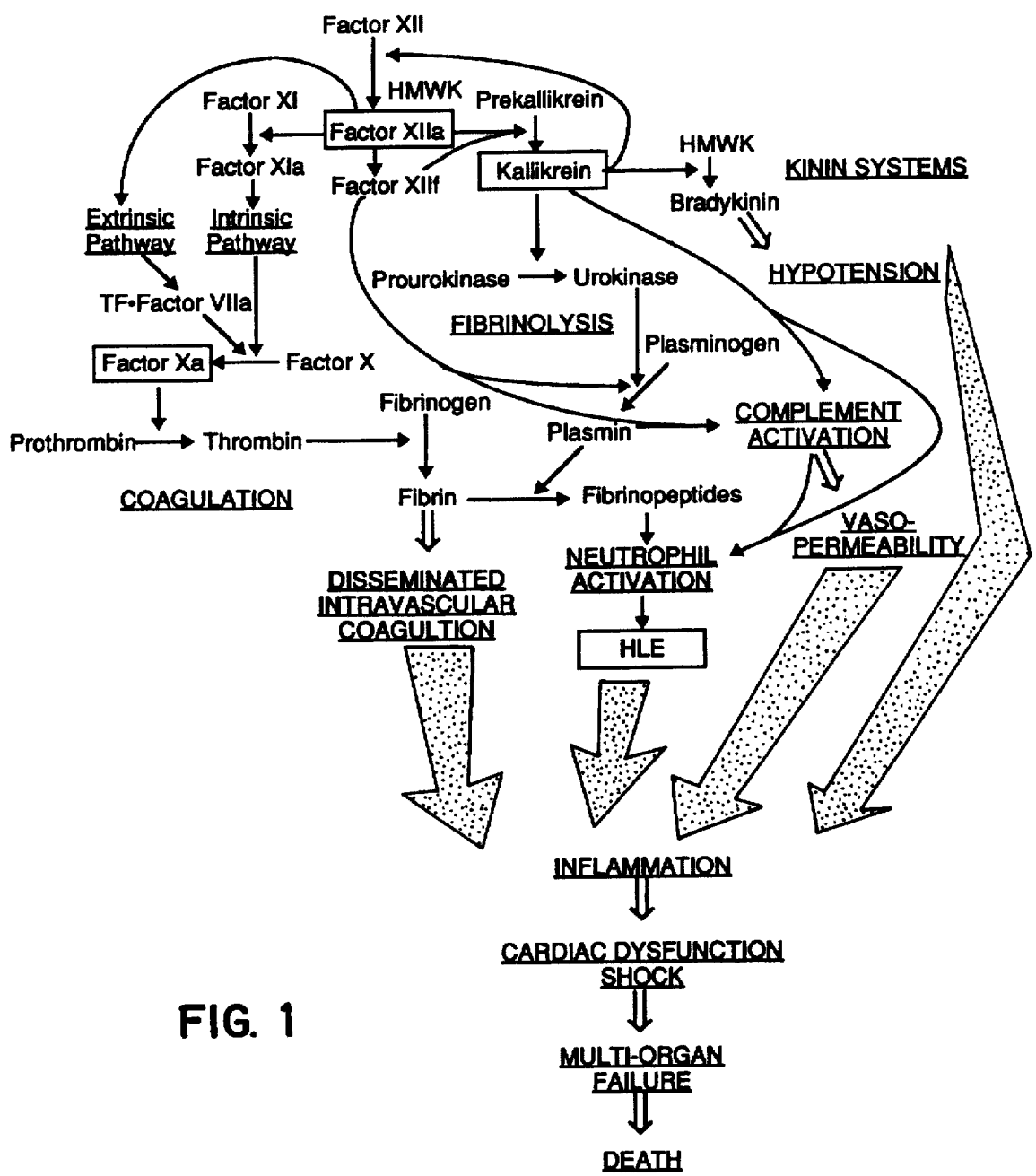
FIG. 1. Schematic outline of selected enzymes and mediators that modulate the contact, coagulation, fibrinolytic, inflammatory, and complement pathways. Serine proteases potently inhibited by ecotin, ecotin homologs and analogs are boxed.

In the course of evaluating various compounds in a Factor Xa, Factor XIIa, plasma kallikrein, and HLE inhibition assays, ecotin, an E. coli periplasmic protein was discovered to be an inhibitor of these enzymes. Ecotin was further tested to determine the affinity as measured by the apparent (K$_i$*) or true (K$_i$) dissociation constant. Ecotin was found to be the most potent known inhibitor of Factor Xa, having a dissociation constant of 17 pM, an association rate constant of $1.35 \times 10^6 M^{-1} s^{-1}$, and a dissociation rate constant of $6.5 \times 10^{-5} s^{-1}$. Ecotin prolonged clotting time about 10-fold at 0.3 µM and at 2 µM in activated partial thromboplastin time and prothrombin time assays respectively. Ecotin did not effectively inhibit the human plasma proteases; thrombin, tissue factor•FVIIa, FXIa, activated protein C, plasmin, or tissue plasminogen activator (t-PA). However it did potently inhibit; Factor XIIa, plasma kallikrein, and human leukocyte elastase (HLE), with K$_i$ values of 25 pM, 41 pM, and 33 pM, respectively. Incubation of ecotin and FXa at 10 µM each resulted in an (ecotin)$_2$•(FXa)$_2$ complex as determined by gel filtration. Dimerization of ecotin alone was measured by fluorescence titration which yielded a K$_d$ of 390 nM. FXa cleaves ecotin slowly at pH 4.0 between Met84 and Met85.

This discovery led to the recombinant production of homologs of ecotin in which various amino acid residues, especially those in the $P^3—P^2—P^1—P^{1'}—P^{2'}$ positions, were substituted. Replacement of the $P_1$ Met84 residue with Arg and Lys led to FXa inhibitors with $K_i$ values of 4 and 7 pM, respectively. The $P_1$ Arg and Lys mutants also significantly inhibited; thrombin, FXIa, activated protein C, plasmin, FXIIa, plasma kallikrein, bovine trypsin and chymotrypsin, but did not inhibit tissue factor•FVIIa, t-PA, or HLE.

A. Definitions

Terms used in the claims and specification are defined as set forth below unless otherwise specified.

The terms $P_1$ and $P^1$ as used herein are interchangeable and refer to the position preceeding the scissile peptide bond of the substrate or inhibitor as previously defined (Schechter, I., & Berger, A., *Biochem. Biophys. Res. Commun.* 27:157–162 [1967]); similarly the terms $P_{1'}$ and $P^{1'}$ are interchangeable and refer to the position following the scissile peptide bond of the substrate or inhibitor. The increasing numbers refer to the next consecutive position preceeding (e.g. $P_2$ and $P^2$) and following (e.g. $P_{2'}$ and $P^{2'}$) the scissile bond.

Ecotin refers to that *E. coli* periplasmic protein having the 142 amino acid residue sequence reported by McGrath, et al., *J. Biol. Chem.* 266:6620–6625 (1991). In this protein, $P^3—P^2—P^1—P^{1'}—P^2—P^{8'}$ correspond to residues 82–87 inclusive and are; Ser, Thr, Met, Met, Ala, and Cys respectively.

Analogs of ecotin refer to proteins found in other species and other genera other than *E. coli* but which are evolutionarily related to ecotin in that they possess a substantially similar primary structure and exhibit substantially similar inhibitory activity toward Factor Xa, Factor XIIa, plasma kallikrein, or HLE. It is reasonable to expect that numerous other species and genera found in the mammialian gut possess proteins which, while not identical to ecotin, serve the same function and have much the same structure. It should be possible to identify, purify, characterize, and produce such analogs using the techniques of the present invention. Analogs preferable have at least about 70% homology to the ecotin amino acid sequences. More preferably analogs have the same $P^3—P^2—P^1—P^{1'}—P^{2'}$ amino acid sequence as ecotin.

Homologs of ecotin refer to synthetically obtained proteins, not known to exist in nature, which possess a primary structure substantially similar to ecotin and which exhibit substantially similar activity toward Factor Xa, Factor XIIa, plasma kallikrein, or HLE. Homologs may be synthetically obtained directly via chemical synthesis, or indirectly via construction of nucleic acid sequences encoding the homolog amino acid sequences followed by use of recombinant DNA techniques to obtain large-scale production of the homologs in culture. Chemically synthesized homologs may contain either L or D α-amino acids, which may be either natural or non-natural amino acids. Homologs preferably have at least about 70% homology to the ecotin amino acid sequence.

In defining homology, the protein resulting from the substitution of an amino acid in the ecotin amino acid sequence by a conservative amino acid substitution is considered to be a homologous protein. Conservative amino acid substitution is defined as the amino acid substitution sets set forth in Table 1 on page 240 of Taylor, W, R., *J. Mol. Biol.*, 188:233–258 (1986). Briefly, the largest recognized categories or sets of conservative amino acid substitutions include; positive (R, K, H), charged (D, E, R, K, H), polar (T, S, N, D, E, Q, R, K, H, W, Y), tiny (A, G, S), small (P, V, C, A, G, T, S, N, D), aliphatic (L, I, V), hydrophobic (H, W, Y, F, M, L, I, V, C, A, G, T, K), and aromatic (F, H, Y, W). See this reference for category refinements and additional categories.

In addition, insertions or deletions of amino acids may occur within homologous proteins. Prefered deletions of the present invention are one or more sequential deletions begining with amino terminal residue 1 continuing through residue 49, just before Cys50, and/or begining with carboxy terminal residue 142, ending at residue 88, just before Cys87.

The term amino acid or amino acid residue, as used herein, refers to naturally-occurring L α-amino acids or residues, unless otherwise specifically indicated. The commonly used one- and three-letter abbreviations for amino acids are use herein (Lehninger, A. L., *Biochemistry*, 2d ed., pp. 71–92, (1975), Worth Publishers, N.Y.).

"Expression vector" refers to a DNA construct containing a DNA sequence which is operably linked to a suitable control sequence capable of effecting the expression of the protein encoded by the DNA in a suitable host. Such control sequences generally include a promoter to effect transcription, an optional operator sequence to control transcription, a sequence encoding suitable mRNA ribosome binding sites, and sequences which control termination of transcription and translation. The vector may be a plasmid, a phage particle or "phagemid", or simply a potential genomic insert.

Once transformed into a suitable host, the vector may replicate and function independently of the host genome, or may, in some instances, integrate into the genome itself. In the present specification, "plasmid", "vector" and "phagemid" are sometimes used interchangeably as the plasmid is the most commonly used form of vector at present. However, the invention is intended to include such other forms of expression vectors which serve equivalent functions and which are, or which become, known in the art.

"Operably linked," when describing the relationship between two DNA or polypeptide sequences, simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The abbreviations used herein are: FXa, Factor Xa; FXIIa, Factor XIIa; HLE, human leukocyte elastase; TF, tissue factor; TFPI, tissue factor pathway inhibitor; ATIII, Antithrombin III; DIC, disseminated intravascular coagulation; ARDS, adult respiratory distress syndrome; HMWK, high molecular weight kininogen; TAP, tick anticoagulant peptide; PCR, polymerase chain reaction; MUGB, 4-methylumbelliferyl p-guanidinobenzoate; 50 mM Tris, pH 7.5, 150 mM NaCl, 2 mM $CaCl_2$, 0.005% Triton X-100, TNCT buffer; CHAPS, 3-[(3-cholamidopropyl) dimethylammonio]-1-propanesulfonate; PBS, phosphate buffered saline, SDS, sodium dodecyl sulfate; PAGE, polyacrylamide gel electrophoresis; TFA, trifluoroacetic acid; HPLC, high performance liquid chromatography; BAPA, $N^\alpha$-Benzoyl-L-arginine-p-nitroanilide; DEAE, diethylaminoethyl; PVDF, polyvinylidene difluoride; PT, prothrombin time; APTT, activated partial thromboplastin time.

B. Utility

As previously indicated, many common human disorders are characteristically associated with a hypercoagulable state leading to intravascular thrombi and emboli. These are a major cause of medical morbidity, leading to phlebitis, infarction, and stroke, and of mortality, from stroke and pulmonary and cardiac emboli. A large percentage of such patients have no antecedent risk factors, and develop venous thrombophlebitis and subsequent pulmonary emboli without a known cause. Other patients who form venous thrombi have underlying diseases known to predispose to these syndromes.

Some of these patients may have genetic or acquired deficiencies of factors that normally prevent hypercoagulability, such as antithrombin III. Others have mechanical obstructions to venous flow, such as tumor masses, that lead to low flow states and thrombosis. Patients with malignancy have a high incidence of thrombotic phenomena, for unclear reasons. Antithrombotic therapy in this situation with currently available agents is dangerous and often ineffective.

Patients with atherosclerosis are predisposed to arterial thromboembolic phenomena for a variety of reasons. Atherosclerotic plaques form niduses for platelet plugs and thrombi that lead to vascular narrowing and occlusion, resulting in myocardial and cerebral ischemic disease. Thrombi that break off and are released into the circulation can cause infarction of different organs, especially the brain, extremities, heart and kidneys. After myocardial infarctions, clots can form in weak, poorly functioning cardiac chambers and be released into the circulation to cause emboli. All such patients with atrial fibrillation are felt to be at great risk for stroke and require antithrombotic therapy.

In addition, thrombolytic therapy for acute myocardial infarction has become an established procedure for patients (Collen, D. and Stump, D. (1988) Ann Rev Med. 39:405–423). However, currently available thrombolytic agents are not effective in all patients which is manifest by reocclusion, resistance to reperfusion, prolonged times to achieve normal coronary flow and the like.

Patients whose blood flows over artificial surfaces, such as prosthetic synthetic cardiac valves or hip replacements, or through extracorporeal perfusion devices, are also at risk for the development of platelet plugs, thrombi, and emboli. It is standard practice that patients with artificial cardiac valves be chronically anti-coagulated.

Thus, a large category of patients, including those with cancer, atherosclerosis, coronary artery disease (PTCA, CABG, Post MI, etc.), unstable angina, artificial heart valves, and a history of stroke, transient ischemic attacks, deep vein thrombosis, phlebitis, or pulmonary emboli, are candidates for limited or chronic antithrombotic therapy. However, this therapy is often ineffective or morbid in its own right. This is partially because the number of available therapeutic agents is limited. Available antiplatelet agents, such as aspirin, inhibit the cyclooxygenase-induced activation of platelets only and are often inadequate for therapy. Available anticoagulants include heparin and warfarin which are not always efficacious and can often have side effects including increased bleeding risk and problems associated with monitoring these therapies.

An agent which effectively inhibits the formation of fibrin from fibrinogen should accordingly be particularly useful in therapeutic intervention in a large group of disorders characterized by a hypercoagulable state.

As a general matter, however, in the management of thromboembolic and inflammatory disorders, the compounds of the present invention may be utilized in compositions with a pharmaceutically acceptable excipient for injectible administration, in compounds such as tablets, capsules, or elixirs for oral administration. Animals in need of treatment using compounds of the present invention can be administered dosages that will provide optimal efficacy. The dose and method of administration will vary from animal to animal, and be dependent upon such factors as weight, diet, concurrent medication, and other factors which those skilled in the medical arts will recognize.

FXa is an appropriate target for intervention in coagulation processes because it is a participant in both the extrinsic and intrinsic pathways (see FIG. 1). In the extrinsic pathway, Factor X is converted to FXa by FVIIa in the presence of tissue factor, phospholipid, and $Ca^{+2}$. In the intrinsic pathway, Factor X is activated to FXa by FIXa in the presence of FVIII, phospholipid, and $Ca^{+2}$. By whatever mechanism of activation, one of the important functions of FXa is its participation in the prothrombinase complex. In concert with FVa, phospholipid, and $Ca^{+2}$, FXa acts as the catalytic moiety that cleaves prothrombin to thrombin, which generates fibrin from fibrinogen, finally resulting in a fibrin clot. Thus, the inhibition of FXa by agents such as ecotin and ecotin homologs represents an approach for clinical intervention in various thrombotic disorders. Thus the ecotin and ecotin homologs of this invention are useful in the treatment of thrombosis. More specifically, the instant inhibitors are especially useful as adjunct therapy for thrombolysis, unstable angina, deep vein thrombosis, coronary artery bypass graft, percutaneous transluminal coronary angioplasty, and DIC.

Ecotin and ecotin homologs of this invention are also useful in the treatment of diseases where intervention in the activation of the contact pathway or neutrophil activation is indicated (e.g. inflammation, coagulation, fibrinolysis, and complement activation). More specifically, the instant inhibitors are especially useful in the treatment of diseases where inhibition of FXIIa, kallikrein, FXa, and HLE is indicated as for example in the treatment of sepsis or septic shock, inflammation, ARDS, DIC, hypotension, cardiopulmonary bypass surgery, and for bleeding from postoperative surgery.

Ecotin and ecotin homologs of this invention may be useful in clinical situations that require acute or chronic therapy. It is anticipated that indications for which acute therapy is indicated are more preferred than those for chronic therapy. The pharmaceutical use of foreign proteins derived from bacterial sources such as *E. coli* may be immunogenic; however bacterial proteins are used to treat acute indications. An example of such a protein is streptokinase, a protein derived from streptococci that acts as a fibrinolytic and is commonly used to treat acute myocardial infarction. Ecotin and ecotin homologs of this invention may elicit an immune response, however we may be immunized against ecotin since *E. coli* are commonly found in the mammalian gut and ecotin can be secreted into the periplasm. The covalent attachment of polyethylene glycol (PEG) to ecotin and ecotin homologs may reduce the immunogenicity and toxicity, and prolong the half-life as has been observed with other proteins (Katre N. V., *J. Immunol.* 144:209–213 [1990]; Poznansky, M. J. et al., FEB 239:18–22 [1988]; Abuchowski, A. et al., *J. Biol. Chem.* 252:3582–3586 [1977])

C. Methods of Making

Chemical Synthesis

One method of producing ecotin and ecotin analogs involves chemical synthesis of the protein, followed by treatment under oxidizing conditions appropriate to obtain the native conformation, that is, the correct disulfide bond linkages. This can be accomplished using methodologies well known to those skilled in the art (see Kelley, R. F. & Winkler, M. E. in *Genetic Engineering Principles and Methods*, Setlow, J. K., ed., Plenum Press, N.Y., vol. 12, pp 1–19 [1990]; Stewart, J. M. & Young, J. D. *Solid Phase Peptide Synthesis* Pierce Chemical Co. Rockford, Ill[1984]).

Figure 2:
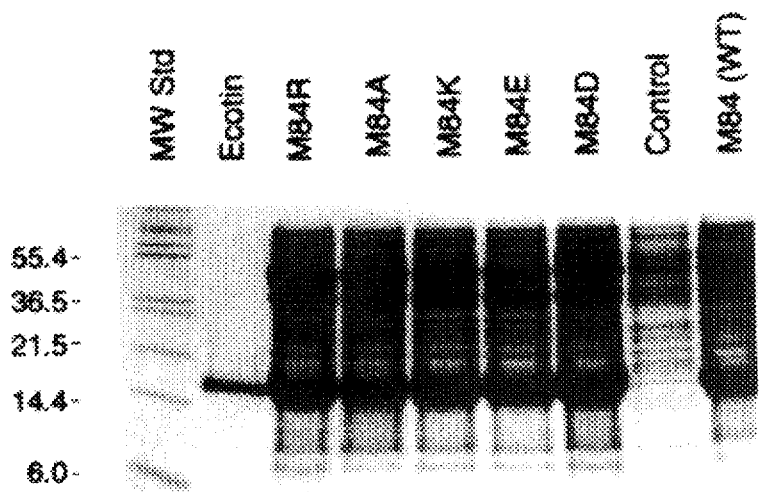
FIG. 2. SDS-PAGE of purified ecotin and crude periplasmic proteins from E. coli transformed with ecotin plasmids. Lane 1, molecular weight markers with the associated Mr values ×10$^{-3}$. Lane 2, purified recombinant ecotin, 4 µg. Lanes 3–7, 25 µl periplasmic contents from ecotin mutant cultures; sample preparation described in text. Lane 8, 27C7 control (no plasmid). Lane 9, 25 µl periplasmic contents from wild type ecotin culture. Samples were reduced with β-mercaptoethanol prior to loading, and the gel was stained with Coomassie Blue.

Polypeptides of the invention, especially those containing fewer than 50 amino acid residues (see Formula VI), may be prepared using solid phase peptide synthesis (Merrifield, *J. Am. Chem. Soc.*, 85:2149 [1964]; Houghten, *Proc. Natl. Acal. Sci. USA* 82:5132 [1985]). Solid phase synthesis begins at the carboxy-terminus of the putative peptide by coupling a protected amino acid to a suitable resin, as shown in FIGS. 1-1 and 1-2, on pages 2 and 4 of Stewart and Young supra.

In synthesizing polypeptides of this invention, the carboxyl terminal amino acid, with its α-amino group suitably protected, is coupled to a chloromethylated polystyrene resin (see FIG. 1-4, page 10 of Stewart and Young supra.). After removal of the α-amino protecting group with, for example, trifluoroacetic acid (TFA) in methylene chloride and neutralizing in, for example TEA, the next cycle in the synthesis is ready to proceed.

The remaining α-amino and, if necessary, side-chain-protected amino acids are then coupled sequentially in the desired order by condensation to obtain an intermediate compound connected to the resin. Alternatively, some amino acids may be coupled to one another forming a peptide prior to addition of the peptide to the growing solid phase polypeptide chain.

The condensation between two amino acids, or an amino acid and a peptide, or a peptide and a peptide can be carried out according to the usual condensation methods such as azide method, mixed acid anhydride method, DCC (dicyclohexylcarbodiimide) method, active ester method (p-nitrophenyl ester method, BOP [benzotriazole-1-yl-oxy-tris (dimethylamino) phosphonium hexafluorophosphate] method, N-hydroxysuccinic acid imido ester method, etc.), and Woodward reagent K method. In the case of elongating the peptide chain in the solid phase method, the peptide is attached to an insoluble carrier at the C-terminal amino acid. For insoluble carriers, those which react with the carboxy group of the C-terminal amino acid to form a bond which is readily cleaved later, for example, halomethyl resin such as chloromethyl resin and bromomethyl resin, hydroxymethyl resin, aminomethyl resin, benzhydrylamine resin, and t-alkyloxycarbonyl-hydrazide resin can be used.

Common to chemical syntheses of peptides is the protection of the reactive side-chain groups of the various amino acid moieties with suitable protecting groups at that site until the group is ultimately removed after the chain has been completely assembled. Also common is the protection of the α-amino group on an amino acid or a fragment while that entity reacts at the carboxyl group followed by the selective removal of the α-amino-protecting group to allow subsequent reaction to take place at that location. Accordingly, it is common that, as a step in the synthesis, an intermediate compound is produced which includes each of the amino acid residues located in the desired sequence in the peptide chain with various of these residues having side-chain protecting groups. These protecting groups are then commonly removed substantially at the same time so as to produce the desired resultant product following purification.

The applicable protective groups for protecting the α-and ε-amino side chain groups are exemplified by benzyloxycarbonyl (abbreviated Z), isonicotinyloxycarbonyl (iNOC), O-chlorobenzyloxycarbonyl [Z(NO₂)], p-methoxybenzyloxycarbonyl [Z(OMe)], t-butoxycarbonyl, (Boc), t-amyioxycarbonyl (Aoc), isobornyloxycarbonyl, adamatyloxycarbonyl, 2-(4-biphenyl)-2-propyloxycarbonyl (Bpoc), 9-fluorenylmethoxycarbonyl (Fmoc), methylsulfonylethoxycarbonyl (Msc), trifluoroacetyl, phthalyl, formyl, 2-nitrophenylsulphenyl (NPS), diphenylphosphinothioyl (Ppt), dimethylophosphinothioyl (Mpt) and the like.

As protective groups for carboxy group there can be exemplified, for example, benzyl ester (OBzl), cyclohexyl ester (Chx), 4-nitrobenzyl ester (ONb), t-butyl ester (Obut), 4-pyridylmethyl ester (OPic), and the like. It is desirable that specific amino acids such as arginine, cysteine, and serine possessing a functional group other than amino and carboxyl groups are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2, 6-dimethylbenzenesulfonyl (Mds), 1,3,5-trimethylphenysulfonyl (Mts), and the like. The thiol group in cysteine may be protected with p-methoxybenzyl, triphenylmethyl, acetylaminomethyl ethylcarbamoyle, 4-methylbenzyl, 2,4,6-trimethy-benzyl (Tmb) etc, and the hydroxyl group in the serine can be protected with benzyl, t-butyl, acetyl, tetrahydropyranyl etc.

Stewart and Young supra provides detailed information regarding procedures for preparing peptides. Protection of α-amino groups is described on pages 14–18, and side-chain blockage is described on pages 18–28. A table of protecting groups for amine, hydroxyl and sulfhydryl functions is provided on pages 149–151.

After the desired amino acid sequence has been completed, the intermediate peptide is removed from the resin support by treatment with a reagent, such as liquid HF and one or more thio-containing scavengers, which not only cleaves the peptide from the resin, but also cleaves all the remaining side-chain protecting groups. Following HF cleavage, the protein sequence is washed with ether, transferred to a large volume of dilute acetic acid, and stirred at pH adjusted to about 8.0 with ammonium hydroxide.

Preferably in order to avoid alkylation of residues in the polypeptide, (for example, alkylation of methionine, cysteine, and tyrosine residues) a thio-cresol and cresol scavenger mixture is used. The resin is washed with ether, and immediately transferred to a large volume of dilute acetic acid to solubilize and minimize intermolecular cross-linking. A 250 µM polypeptide concentration is diluted in about 2 liters of 0.1M acetic acid solution. The solution is then stirred and its pH adjusted to about 8.0 using ammonium hydroxide. Upon pH adjustment, the polypeptide takes its desired conformational arrangement.

Gene Synthesis, Cloning, and Expression

General Procedures

From the purified protein and its amino acid sequence, ecotin or ecotin homologs may be produced using recombinant DNA techniques. These techniques contemplate, in simplified form, taking a gene encoding either ecotin or ecotin homologs; inserting it into an appropriate vector; inserting the vector into an appropriate host cell; culturing the host cell to cause expression of the ecotin or ecotin homolog gene; and purifying the protein produced thereby.

Somewhat more particularly, the DNA sequence encoding either ecotin or a ecotin homolog is cloned and manipulated so that it may be expressed in a convenient host. DNA encoding parent polypeptides can be obtained from a genomic library, from cDNA derived from mRNA from cells expressing ecotin or ecotin homologs, or by synthetically constructing the DNA sequence (Sambrook, J. et al., *Molecular Cloning* (2nd ed.), Cold Spring Harbor Laboratory, N.Y. [1989]).

The parent DNA is then inserted into an appropriate plasmid or vector which is used to transform a host cell. In general, plasmid vectors containing replication and control sequences which are derived from species compatible with the host cell are used in connection with those hosts. The vector ordinarily carries a replication site, as well as sequences which encode proteins that are capable of providing phenotypic selection in transformed cells.

For example, *E. coli* may be transformed using pBR322, a plasmid derived from an *E. coli* species (Mandel, M. et al., *J. Mol. Biol.* 53:154 [1970]). Plasmid pBR322 contains genes for ampicillin and tetracycline resistance, and thus provides easy means for selection. Other vectors include different features such as different promoters, which are often important in expression. For example, plasmids pKK223-3, pDR720, and pPL-lambda represent expression vectors with the tac, trp, or PL promoters that are currently available (Pharmacia Biotechnology).

Direct Expression of Ecotin or an Ecotin Homolog

A preferred vector is pet3. This vector was created as described in Example 1 and contains origins of replication for *E. coli*, the alkaline phosphatase promoter, the ecotin signal sequence and gene, and the ampicillin resistance gene. Other preferred vectors are pBO475, pR1T5 and pR1T2T (Pharmacia Biotechnology). These vectors contain appropriate promoters followed by the Z domain of protein A, allowing genes inserted into the vectors to be expressed as fusion proteins. Further discussion of these vectors may be found below.

Other preferred vectors can be constructed using standard techniques by combining the relevant traits of the vectors described herein as illustrated in Example 3. In this instance a vector containing the origins of replication for phage and *E. coli*, which allow it to be shuttled between such hosts, was used thereby facilitating both mutagenesis and expression (Cunningham, B., et al., *Science* 243:1330–1336 [1989]; Wells, J. & Cunningham, B., co-pending application U.S. Ser. No. 07/428,066 filed 26 Oct. 1989). Relevant traits of the vector include the promoter, the ribosome binding site, the ecotin or ecotin homolog gene or gene fusion (the Z domain of protein A and ecotin or an ecotin homolog and its linker), the signal sequence, the antibiotic resistance markers, the copy number, and the appropriate origins of replication.

Ecotin has been expressed in *E coli* using a plasmid with the tac promoter and the lacI$^q$ repressor gene. This resulted in an inducible expression system capable of expressing greater than 400 mg/L of ecotin (McGrath, M. E. et al., *J. Mol. Biol.* 222:139–142 [1991]).

The host cell may be prokaryotic or eukaryotic. Prokaryotes are preferred for cloning and expressing DNA sequences to produce parent polypeptides, segment substituted polypeptides, residue-substituted polypeptides and polypeptide variants. For example, *E. coli* K12 strain 294 (ATCC No. 31446) may be used as *E. coli* B, *E. coli* X1776 (ATCC No. 31537), and *E. coli* c600 and c600hfl, *E. coli* W3110 (F-, gamma-, prototrophic/ATCC No. 27325), bacilli such as *Bacillus subtilis*, and other enterobacteriaceae such as *Salmonella-typhimurium* or *Serratia marcesans*, and various pseudomonas species. The preferred prokaryote is *E. coli* W3110 (ATCC 27325). When expressed by prokaryotes the polypeptides typically contain an N-terminal methionine or a formyl methionine and are not glycosylated. In the case of fusion proteins, the N-terminal methionine or formyl methionine resides on the amino terminus of the fusion protein or the signal sequence of the fusion protein. These examples are, of course, intended to be illustrative rather than limiting.

In addition to prokaryotes, eukaryotic organisms, such as yeast cultures, or cells derived from multicellular organisms may be used. In principle, any such cell culture is workable. However, interest has been greatest in vertebrate cells, and propagation of vertebrate cells in culture (tissue culture) has become a reproducible procedure (*Tissue Culture*, Academic Press, Kruse and Patterson, editors (1973)). Examples of such useful host cell lines are VERO and HeLa cells, Chinese Hamster Ovary (CHO) cell lines, W138, 293, BHK, CO-7 and MDCK cell lines.

Specifically, in the instant case, the ecotin gene was cloned by PCR using *E. coli* chromosomal DNA and synthetic primers based upon the published coding sequence (McGrath, M. E. et al., *J. Biol. Chem*, supra; Lee, H. R. et al.,*FEBS Lett* 287:53–56 [1991]), and inserted into a convenient expression vector. The resulting plasmid, pEt3, places the transcription of the ecotin gene under the control of the alkaline phosphatase promoter (AP) and translation under control of the tryptophan Shine-Dalgarno sequence. The endogenous ecotin signal sequence was used for efficient secretion of ecotin into the *E. coli* periplasm.

Gene Fusions

A variation on the above procedures contemplates the use of gene fusions, wherein the gene encoding the ecotin or ecotin homolog is associated, in the vector, with a gene encoding another protein or a fragment of another protein. This results in ecotin or an ecotin homolog being produced by the host cell as a fusion with another protein. The "other" protein is often a protein or peptide which can be secreted by the cell, making it possible to isolate and purify the desired protein from the culture medium and eliminating the necessity of destroying the host cells which arises when the desired protein remains inside the cell. Alternatively, the fusion protein can be expressed intracellularly. It is useful to use fusion proteins that are highly expressed.

The use of gene fusions, though not essential, can facilitate the expression of heterologous proteins in *E. coli* as well as the subsequent purification of those gene products (Harris, T. J. R. in *Genetic Engineering*, Williamson, R., Ed., Academic, London, Vol. 4, p. 127 [1983]; Uhlen, M. & Moks, T., *Methods Enzymol.* 185:129–143 [1990]). Protein A fusions are often used because the binding of protein A, or more specifically the Z domain of protein A, to IgG provides an "affinity handle" for the purification of the fused protein (Nilsson, B. & Abrahmsen, L. *Methods Enzymol.* 185:144–161 [1990]). It has also been shown that many heterologous proteins are degraded when expressed directly in *E. coli*, but are stable when expressed as fusion proteins (Marston, F. A. O., *Biochem J.* 240:1 [1986]).

Ecotin or ecotin homologs expressed as fusion proteins may be properly folded or may require folding to obtain the native structure. The properly folded fusion protein may be active and useful as a serine protease inhibitor. More preferred would be the correctly folded native protein that is obtained from the fusion protein by methods known in the art. Fusion proteins can be cleaved using chemicals, such as cyanogen bromide, which cleaves at a methionine, or hydroxylamine, which cleaves between an Asn and Gly. Using standard recombinant DNA methodology, the nucleotide base pairs encoding these amino acids may be inserted just prior to the 5' end of the ecotin or ecotin homolog gene.

Alternatively, one can employ proteolytic cleavage of fusion proteins, which has been recently reviewed (Carter, P. (1990) in *Protein Purification: From Molecular Mechanisms to Large-Scale Processes*, Ladisch, M. R., Willson, R. C., Painton, C. C., and Builder, S. E., eds., American Chemical Society Symposium Series No. 427, Ch 13, 181–193).

Proteases such Factor Xa, thrombin, subtilisin and mutants thereof, have been successfully used to cleave fusion proteins. Typically, a peptide linker that is amenable to cleavage by the protease used is inserted between the "other" protein (e.g., the Z domain of protein A) and the protein of interest, such as ecotin or an ecotin homolog. Using recombinant DNA methodology, the nucleotide base pairs encoding the linker are inserted between the genes or gene fragments coding for the other proteins. Proteolytic cleavage of the partially purified fusion protein containing the correct linker can then be carried out on either the native fusion protein, or the reduced or denatured fusion protein.

The protein may or may not be properly folded when expressed as a fusion protein. Also, the specific peptide linker containing the cleavage site may or may not be accessible to the protease. These factors determine whether the fusion protein must be denatured and refolded, and if so, whether these procedures are employed before or after cleavage.

When denaturing and refolding are needed, typically the protein is treated with a chaotrope, such a guanidine HCl, and is then treated with a redox buffer, containing, for example, reduced and oxidized dithiothreitol or glutathione at the appropriate ratios, pH, and temperature, such that the protein of interest is refolded to its native structure.

Mutant DNA Production

As previously discussed, various techniques are also available which may now be employed to produce mutant ecotin or ecotin homolog DNA, which encodes for additions, deletions, or changes in amino acid sequence of the resultant protein relative to the parent ecotin molecule.

By way of illustration, with expression vectors encoding ecotin in hand, site specific mutagenesis (Kunkel et al., *Methods Enzymol.* 204:125–139 [1991]; Carter, P., et al., *Nucl. Acids. Res.* 13:4331 [1986]; Zoller, M. J. et al.,*Nucl. Acids Res.* 10:6487 [1982]), cassette mutagenesis (Wells, J. A., et al.,*Gene* 34:315 [1985]), restriction selection mutagenesis (Wells, J. A., et al., *Philos. Trans, R. Soc. London SerA* 317, 415 [1986]) or other known techniques may be performed on the ecotin DNA. The mutant DNA can then be used in place of the parent DNA by insertion into the aforementioned expression vectors. Growth of host bacteria containing the expression vectors with the mutant DNA allows the production of mutant ecotin (i.e., analogs or homologs of ecotin), which can be isolated as described herein.

Specifically, in the present case, several mutants of ecotin that substituted the $P_1$ residue Met84 with Arg, Lys, Ala, Glu, or Asp resulted in mutants that were expressed at comparable levels to wild type ecotin (FIG. 2). Cultures of *E. coli* strain 27C7 containing the ecotin expression plasmids were grown in shake flasks for 20 h at 37° C. in a low phosphate minimal media. Based on SDS-PAGE, we estimate ecotin homologs represents ~15% of the total periplasmic protein (see FIG. 2).

Purification and Characterization

Purification and characterization of ecotin and ecotin homologs may be carried out by any art standard technique. In the instant case, recombinant ecotin was purified from the periplasm of *E. coli* grown in 10 l fermentors by chromatography on DEAE-Sepharose, reverse phase C18 resin, Superdex size exclusion resin, and Q-Sepharose. Approximately 650 mg of ecotin per 100 g wet cell paste was isolated using this method. We also purified recombinant ecotin and ecotin mutants or homologs from shake flasks by chromatography on a trypsin affinity column followed by reverse phase C18 HPLC. The trypsin affinity/C18 HPLC scheme, when used to purify the ecotin and ecotin mutants, resulted in ~1 mg of isolated protein per liter of culture. Purification of the M84R and M84 K mutants yielded only ~0.1 mg isolated protein per liter of culture, due to cleavage of ecotin at $P_1$ (Lys or Arg) by the immobilized trypsin; the cleaved protein was readily resolved from intact material by HPLC.

Purified recombinant ecotin appeared to be identical to the endogenous ecotin based on comparisons of mass spectral data (16099.3 amu, obs.; 16099.5 amu, calcd.) and amino acid analysis with published values. The purified ecotin appeared to be >95% homogeneous based on SDS-PAGE (FIG. 2, Lane 2) and reverse phase HPLC. Mass spectral analysis of the purified M84R, M84K, M84A, M84D, and M84E homologs revealed masses within 2 amu for the respective calculated theoretical masses for each protein. Amino acid analysis of the mutants was within experimental error of that calculated from the sequence.

D. METHODS OF ANALYSIS

General Activity Assays

Routine enzyme inhibition assays were conducted in a microtiter format and absorbance changes were monitored on an SLT EAR340AT plate reader which was controlled by a Macintosh SE computer equipped with Biometallics DeltaSoftII SLT software. Nonlinear regression analysis was carried out using KaleidaGraph v2.1.4. (Synergy Software).

Ecotin activity and quantitation was carried out using trypsin, which was previously quantitated by burst titration (see below). Trypsin inhibition was measured under the following conditions: 10 nM trypsin, 25 µl 10X trypsin buffer (500 mM Tris, pH 8.0, 100 mM $CaCl_2$), and inhibitor plus water to a total volume of 200 ul. After a 15 min incubation at room temperature, 50 µl 2.5 mM Spectrozyme fXa was added and the absorbance at 405 nm was recorded.

Inhibition of FXa was measured under the following conditions: 5 nM human FXa, 25 µl 10X TNCT buffer (500 mM Tris, pH 7.5, 1.5M NaCl, 20 mM $CaCl_2$, 0.05% Triton X-100) and inhibitor plus water to a total volume of 200 ul. After a 15 min incubation at room temperature, 50 µl 25 mM Spectrozyme fXa was added and the absorbance at 405 nm was recorded.

N-Terminal Sequence Analysis, Mass Spectrometry, and Amino Acid Analysis

Sequential Edman degradation was performed directly on the PVDF membrane on a model 470A Applied Biosystems gas phase sequencer equipped with a 120A PTH amino acid analyzer. PTH amino acid peaks were integrated with Nelson Analytical model 3000 data system; data analysis was performed on a Vax 11/785 Digital Equipment System according to the method of Henzel et al. (Henzel, W. J. et al., *J. Chromatogr.* 404:41–52 [1987]).

Electrospray mass spectra were obtained using a Sciex API-III triple quadropole mass spectrometer equipped with the Ionspray interface operating at 5 kV and calibrated with a solution of polypropylene glycols.

Protein samples were hydrolyzed under vacuum with constant boiling 6N HCl vapor in the Millipore Picotag system for 20 hours at 110° C. The hydrolysates were vacuum evaporated in a Savant speed vac concentrator, and analyzed on a Beckman model 6300 amino acid analyzer equipped with a ninhydrin detector.

Determination of Equilibrium Inhibition Constants

Apparent $K_i$ values ($K_i^*$) for the inhibition of the enzymes tested by ecotin and mutants were measured as follows. All reactions were performed at 25° C. Stock solutions of trypsin were quantitated by active site burst titration with MUGB as previously described (Jameson, G. W. et al., Biochem. J. 131:107–117 [1973]) using a Fluoroskan II plate reader at excitation wavelength of 355 nm and emission wavelength of 460 nm. Data was collected on a Macintosh SE20 using either Delta Soft II F1 v3.31 software (BioMetallics). Active site titrated trypsin was then used to quantitate ecotin active sites using BAPA as the substrate; a stoichiometry of 1:1 was assumed (Chung, C. H. et al., supra). Factor Xa, Factor XIIa, plasma kallikrein, or HLE were then quantitated by active site titration using ecotin as a standard, again assuming 1:1 stoichiometry. In addition, the concentration of HLE was quantitated by methods previously described using a calibrated stock of $\alpha_1$-proteinase inhibitor to titrate the HLE active sites (Beatty, K. et al., J. Biol. Chem. 255:3931–3934 [1980]); the same HLE active site concentration was determined using both ecotin and $\alpha_1$-proteinase inhibitor. The substate for FXa was Spectrozyme fXa (0.5 mM); the substrate for FXIIa (0.5 mM) and plasma kallikrein was S2302 (0.5 mM); the substrate for HLE was MeOSuc-Ala-Ala-Pro-Val-pNA (0.4 mM). There was good agreement upon comparison of the protein concentrations determined by amino acid analysis, Bradford analysis (Bradford, M. M. Anal. Biochem. 72:248–254 (1976) or active site titrations for trypsin, ecotin, FXa, FXIIa, plasma kallikrein, and HLE.

Figure 3:
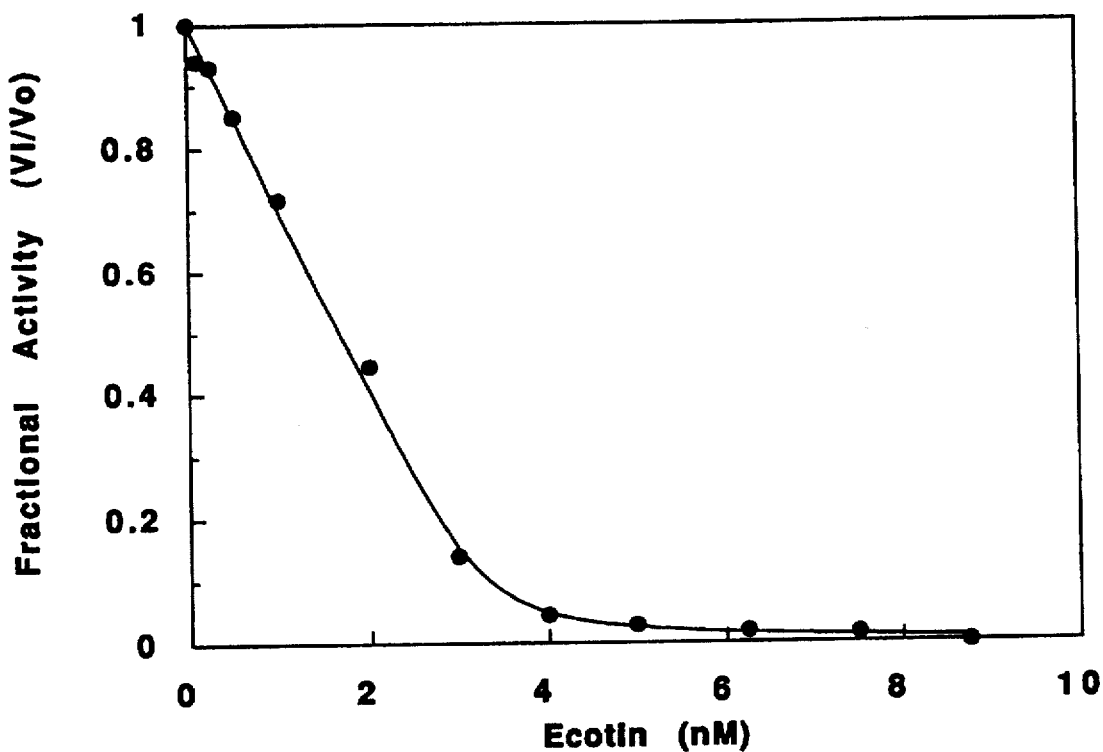
FIG. 3. Determination of apparent equilibrium inhibition constant of ecotin with FXa. Inhibition of FXa by purified wild type ecotin at varying ecotin concentrations. The inhibitory activity is expressed as the ratio of the inhibited rate to the uninhibited rate (fractional activity) at varying inhibitor concentrations at equilibrium. The FXa concentration was 3.3 nM. The apparent equilibrium dissociation value was determined by nonlinear regression analysis of the data to equation 1 and yielded a K$_i$* value of 47 pM. The data shown are typical of three independent determinations.

Since there was significant inhibition at concentrations of ecotin comparable to that of the enzyme, Michaelis-Menton kinetics are not valid. Therefore, apparent equilibrium dissociation values ($K_{i*}$) were determined using methods derived for tight-binding inhibitors (Morrison, J. F. Biochim. Biophys. Acta 185:269–286 [1969]), (Bieth, J. in Proteinase Inhibitors (Fritz, H., Tschesche, H., Greene, L. J. and Truscheit, E., Ed.) pp 463–469, Springer-Verlag, New York [1974]). Data were fit by nonlinear regression analysis to equation 1 and values for $K_i^*$ were determined.

$$\alpha = 1 - \frac{[E_o] + [I_o] + K_i^* - \sqrt{([E_o] + [I_o] + K_i^*)^2 - (4 \cdot [E_o] \cdot [I_o])}}{2 \cdot [E_o]} \quad (1)$$

where $\alpha$ is the fractional activity (steady-state inhibited rate divided by the uninhibited rate), $[E_o]$ is the total enzyme concentration, and $[I_o]$ is the total ecotin concentration. Since the inhibitor and substrate compete for the same site, the true $K_i$ value is related to $K_i^*$ by the expression $K_i = K_i^*/(1+[S]/Km)$, where $K_m$ is the Michaelis constant for the substrate, and $[S]$ is the substrate concentration.

a. Factor Xa Values of $K_i^*$ were determined in triplicate by incubation of various dilutions (0 to 8.7 nM final concentration) of the quantitated ecotin or ecotin mutant in TNCT buffer with human FXa (1 to 5 nM final concentration) in a total volume of 180 ul. Following a 1 hour incubation at room temperature to reach equilibration of the enzyme •inhibitor complex, 20 µl of 5 mM Spectrozyme fXa was added, and the steady-state rate of product formation measured by monitoring the change in absorbance at 405 nm. The $K_m$ for Spectrozyme fXa with FXa under these conditions was determined to be 0.23 mM by linear regression analysis of Lineweaver-Burke plots. The measured $K_i^*$ value for the inhibition of ecotin with FXa was determined in triplicate to be 54±21 pM; the inhibition of FXa by ecotin under equilibrium conditions is shown in FIG. 3. Therefore, a $K_i$ value of 17±7 pM for ecotin binding to FXa was calculated; $K_i$ values for the ecotin mutants are reported in Table I.

b. Factor XIIa Values of $K_i^*$ were determined in triplicate by incubation of various dilutions (0 to 80 nM final concentration) of the quantitated ecotin in buffer (50 mM Tris, pH 7.5, 20 mM NaCl, 2 mM $CaCl_2$, and 0.005% Triton X-100) with human FXIIa (12.5 nM final concentration) in a total volume of 180 ul. Following a 1 hour incubation at room temperature to reach equilibration of the enzyme•inhibitor complex, 20 µl of 5 mM S2302 was added (0.5 mM final concentration), and the steady-state rate of product formation measured by monitoring the change in absorbance at 405 nm. The $K_m$ for S2302 with FXIIa under these conditions was determined to be 0.125 mM by linear regression analysis of Lineweaver-Burke plots.

The measured $K_i^*$ value for the inhibition of ecotin with FXIIa was determined in triplicate to be 124±26 pM; the calculated $K_i$ value was 25±5 pM.

c. Plasma kallikrein Values of $K_i^*$ were determined in triplicate by incubation of various dilutions (0 to 16 nM final concentration) of the quantitated ecotin in buffer (50 mM Tris, pH 7.5, 20 mM NaCl, and 0.005% Triton X-100) with human plasma kallikrein (1.3 or 4.3 nM final concentration) in a total volume of 180 ul. Following a 1 hour incubation at room temperature to reach equilibration of the enzyme.inhibitor complex, 20 µl of 5 mM S2302 was added (0.5 mM final concentration), and the steady-state rate of product formation measured by monitoring the change in absorbance at 405 nm. The $K_m$ for S2302 with plasma kallikrein under these conditions was determined to be 0.165 mM by linear regression analysis of Lineweaver-Burke plots.

The measured $K_i^*$ value for the inhibition of ecotin with human plasma kallikrein was determined in triplicate to be 175±20 pM (plasma kallikrein=1.3 nM) and 151±20 pM (plasma kallikrein=4.3 nM); the calculated $K_i$ values were 44±6 pM and 38±pM, respectively. The average $K_i$ for the inhibition of ecotin with human plasma kallikrein was 41±8 pM.

d. HLE Ecotin (0–5 nM final concentration) was incubated with HLE (0.86 nM) for 2 hours in 0.1M Tris HCl pH 7.5, 0.5M NaCl and 0.005% Triton X-100. MeOSuc-Ala-Ala-Pro-Val-MCA (SEQ ID No. 9) was added (0.08 mM final concentration) and the reaction was monitored on a Labsystems Fluoroskan II plate reader; the excitation wavelenth was 355 nm and the emmission wavelength was 460 nm. Data was collected on a Macintosh SE20 using either Delta Soft II Fl v3.31 software (BioMetallics). The $K_m$ for MeOSuc-Ala-Ala-Pro-Val-MCA (SEQ ID No. 9) with HLE under these conditions was determined to be 0.15 mM by linear regression analysis of Lineweaver-Burke plots.

The measured $K_i^*$ value for the inhibition of ecotin with HLE was determined to be 50 pM; the calculated $K_i$ value was 33 pM.

TABLE I

Kinetic Constants for Ecotin and P₁ Mutants with Factor Xa

| Ecotin Mutant | $K_i$ (pM)[a] | $k_{on} \times 10^{-6}$ ($M^{-1}s^{-1}$)[b] | $k_{off}(s^{-1})$[c] |
|---|---|---|---|
| Wild type | 17 ± 7 | 1.35 ± 0.08 | $6.5 \times 10^{-5}$ ($2.2 \times 10^{-5}$) |
| M84R | 4 | 0.28 ± 0.01 | ($1.0 \times 10^{-6}$) |
| M84K | 7 | 0.68 ± 0.02 | ($4.5 \times 10^{-6}$) |
| M84A | 3900 | 0.17 ± 0.01 | ($6.6 \times 10^{-4}$) |
| M84D | 17700 | N.D.[d] | N.D. |
| M84E | 8210 | 0.07 | ($5.7 \times 10^{-4}$) |

[a]the wild type $K_i$ represents the average of three determinations; the mutant $K_i$ values are from single determinations.
[b]represents the average of three determinations except for M84E which was from a single determination.
[c]values in parenthesis are calculated from $(K_i) \cdot (k_{on})$.
[d]N.D., not determined.

Determination of FXa Association Rate Constants

The association rate of ecotin with FXa was determined as follows. At reference time zero, ecotin (7 nM final concentration) was added to FXa (5 nM final concentration) and TNCT buffer in a total volume of 3.0 ml. Immediately thereafter, 150 μl aliquots were removed at intervals over a period of 10 min and added to microtiter wells containing 50 μl 5 mM Spectrozyme fXa. The absorbance of the wells was monitored at 405 nm. Initial rates were determined for each well using the initial linear portion of each data set. The concentration of free enzyme versus time was plotted and the curves fired to equation 4; values for $k_{on}$ were determined by nonlinear regression analysis.

The rate of association of a reversible inhibitor with enzyme is given by equation 2:

$$\frac{-d[E]}{d(t)} = k_{on} \cdot [E] \cdot [I] - k_{off} \cdot [E \cdot I] \quad (2)$$

Since measurements were made during the initial phase of the reaction, where dissociation of the E.I complex is negligible, the second term of equation 2 can be ignored. Therefore the rate of association is given by equation 3:

$$\frac{-d[E]}{d(t)} = k_{on} \cdot [E] \cdot [I] \quad (3)$$

Figure 4A:
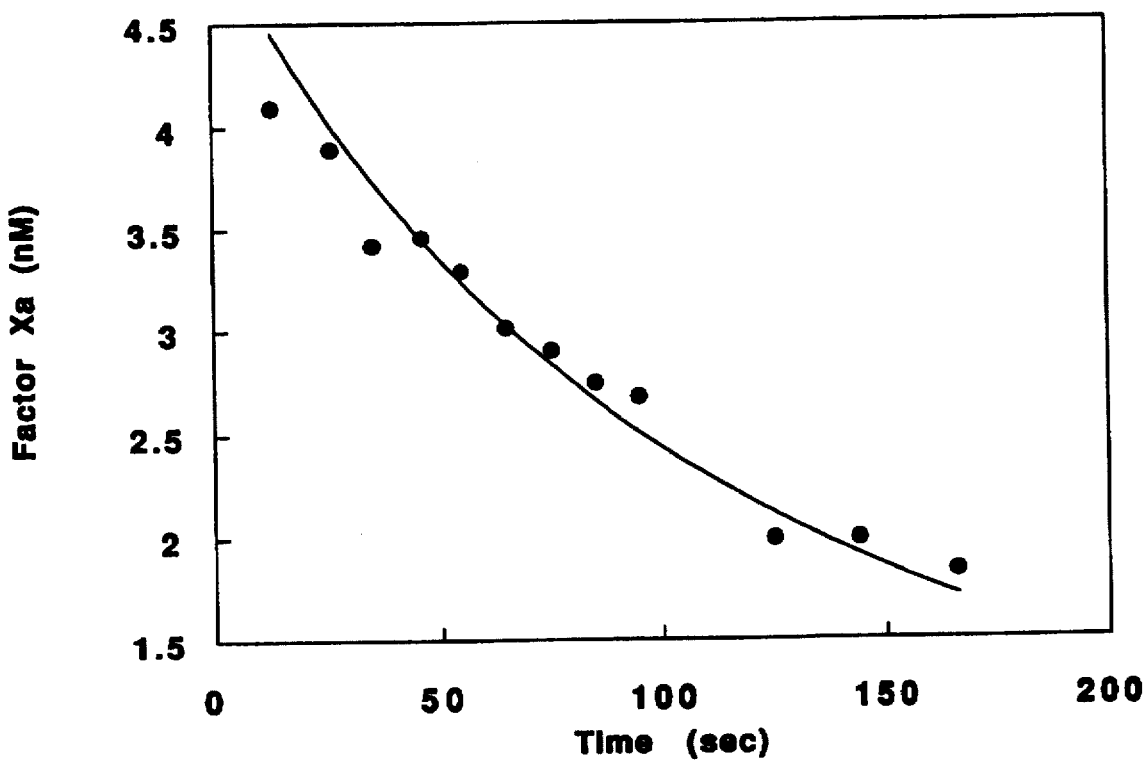
FIGS. 4A and 4B. Determination of Ecotin and FXa association and Ecotin. FXa dissociation rates. Experimental conditions, curve fitting, and rate constant determinations are described in the text.

When Eo≠Io this integrates to equation (4):

$$[E] = [E_o] - \frac{[I_o] \cdot [E_o] \cdot (e^{([I_o]-[E_o]) \cdot k_{on} \cdot t} - 1)}{[I_o] \cdot e^{([I_o]-[E_o]) \cdot k_{on} \cdot t} - [E_o]} \quad (4)$$

where [E] is the concentration of free enzyme at any time t and [E₀] and [I₀] represent the initial concentrations of enzyme and inhibitor, respectively. The association rate constant for ecotin with FXa was determined by measuring free enzyme as a function of time and firing the data to equation (4) by nonlinear regression analysis. A value for $k_{on}=(1.35\pm08)\times 10^6 M^{-1}s^{-1}$ was calculated for ecotin with FXa (FIG. 4A); $k_{on}$ values for ecotin mutants are shown in Table I.

Determination of FXa dissociation rate constant The dissociation rate constant of the ecotin•FXa complex was measured using HLE to trap the free ecotin released from the complex. FXa (10 μM) was incubated for 1 h in TNCT buffer in the presence and absence of ecotin (12.5 μM) and diluted 1000-fold into TNCT buffer with and without HLE (500 nM). Aliquots (180 μl) were removed at various times and initial rates of free FXa were measured at 405 nm with 20 μl of 5 mM Spectrozyme fXa. The product curve (free FXa versus time) was fit to equation 6; the value for $k_{off}$ was determined by nonlinear regression analysis.

Figure 4B:
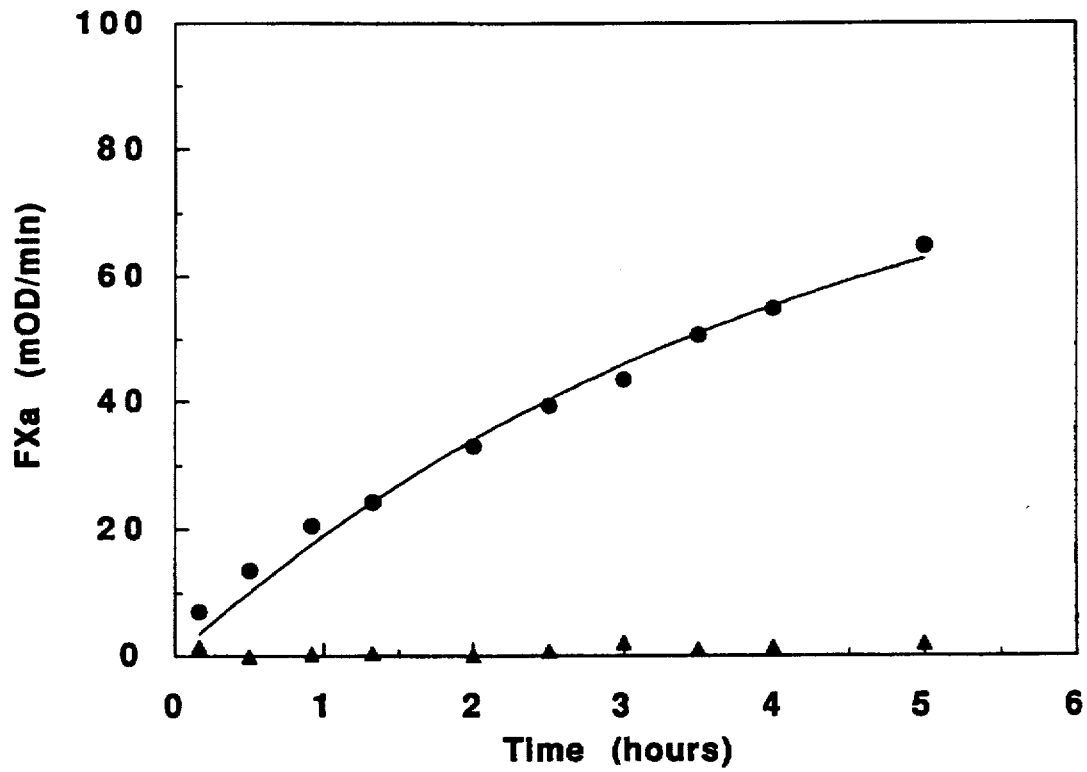

To measure the dissociation rate constant of ecotin from FXa, the complex was diluted 1000-fold into buffer containing a 50-fold excess of HLE to trap the free ecotin and prevent reassociation. In the absence of HLE, reassociation of ecotin with FXa was so rapid that free FXa was barely detectible (FIG. 4B). Progress of dissociation was monitored as the increase in hydrolysis rate of Spectrozyme fXa resulting from the increasing free FXa with time. Because HLE prevented reassociation the rate of dissociation of the E.I complex is given by equation (5):

$$\frac{d[E]}{d(t)} = k_{off} \cdot [E \cdot I] \quad (5)$$

which upon integration gives equation (6):

$$[E]=[E \cdot I]_o \cdot (1-e^{-k_{off} \cdot t}) \quad (6)$$

where [E] is the free [FXa] at any time t, [E•I]₀ is the concentration of the complex at time zero, and $k_{off}$ is the first order dissociation rate constant. The time dependent E•I complex dissociation curve fit to equation (6) by nonlinear regression analysis is shown in FIG. 4B; the dissociation rate constant for ecotin tested is shown above in Table I.

Specificity Assays

The following assays were used to test the specificity of ecotin and the M84K and M84R mutants against various proteases. Ecotin, M84K, M84R (100 nM each), or a control blank were incubated at room temperature for ~1 h with each enzyme. The enzymes tested (enzyme concentration, buffer, substrate) were FXa (1.2 nM, Buffer A, 0.7 mM Spectrozyme fXa), thrombin (3.7 nM, Buffer A, 0.7 mM S2366), TF•FVIIa (12.0 nM, Buffer B, 0.7 mM S2366), FXIa (1.2 nM, Buffer A containing 1 mg/ml BSA, 0.7 mM S2366), activated protein C (4.3 nM, Buffer A, 0.7 mM S2366), plasmin (15 nM, Buffer A, 1 mM S2251), single chain t-PA (15 nM, Buffer A, 2.5 mM S2288), Factor XIIa (10 nM, Buffer A, 0.5 mM S2302, plasma kallikrein (10 nM, Buffer A, 0.5 mM S2302), HLE (17 nM, 0.1M Tris, pH 7.5, 0.5M NaCl and 0.005% Triton X-100, 0.42 mM MeOSuc-AAPV-pNA) (SEQ ID No. 9), bovine trypsin (10 nM, Buffer A, 0.25 mM Spectrozyme fXa), and bovine chymotrypsin (10 nM, Buffer A, 1 mM Suc-AAPF-pNA) (SEQ ID No. 9). Buffer A contains 50 mM Tris, pH 7.5, 100 mM NaCl, 2 mM CaCl₂ and 0.005% Triton X-100. Buffer B contains 50 mM Tris, pH 7.5, 100 mM NaCl, 10 mM CaCl₂, 0.5% BSA, 60 nM TF1–243, and 1 mM CHAPS. The initial change in absorbance at 405 nm was monitored after addition of substrate. Controls lacking inhibitor and/or enzyme were also assayed to assess the uninhibited rates and the background substrate hydrolysis rates, respectively.

In order to investigate the activity and specificity of ecotin more completely, we assayed ecotin and the M84R and M84K P₁ replacement mutants with several other human serine proteases found in plasma. In addition to FXa, ecotin potently inhibited FXIIa and kallikrein, as well as HLE (see above) little or no inhibition was observed with thrombin, TF•FVIIa, FXIa, activated protein C, plasmin, or t-PA (Table II). Changing the P₁ residue to either Arg or Lys led to mutants that were slightly more potent as FXa inhibitors (Table I). However, these mutants also exhibited significant inhibition of thrombin, FXIa, activated protein C, and plasmin. FXIIa and kallikrein were still potently inhibited; however, the introduction of the positively charged Arg or Lys in the P₁ position effectively diminished inhibition of HLE (Table f 1). Neither ecotin, the M84R or M84K mutants inhibited TF•FVIIa or t-PA, whereas bovine trypsin and chymotrypsin were potently inhibited by all of the inhibitors shown in Table II.

TABLE II

Percent Activity of Selected Proteases with Ecotin, M84R, and M84K mutants[a]

| Protease | Ecotin | M84R | M84K |
|---|---|---|---|
| Factor Xa | 0 | 1 | 2 |
| Thrombin | 98 | 4 | 16 |
| TF/Factor VIIa | 99 | 87 | 92 |
| Factor XIa | 79 | 5 | 12 |
| Activated protein C | 99 | 50 | 65 |
| Plasmin | 100 | 10 | 9 |
| t-PA | 100 | 100 | 100 |
| Factor XIIa | 0 | 1 | 0 |
| Kallikrein | 0 | 1 | 2 |
| HLE | 0 | 88 | 85 |
| Trypsin | 0 | 0 | 0 |
| Chymotrypsin | 0 | 0 | 1 |

[a]Conditions for the inhibition assays are described above.

Cleavage of Ecotin by FXa and Active Site Determination

In order to determine if ecotin is cleaved by FXa, enzyme and inhibitor were incubated together at pH 4 and 7.5 essentially as described previously (McGrath, M. E. et al., *J. Biol. Chem,* supra). At various time points, aliquots of the reaction mixture were removed and subjected to SDS-PAGE on 16% Tricine gels. These gels were then electroblotted onto polyvinylidene difluoride (PVDF) membranes, the membranes were stained for 30 seconds in 0.1% Coomassie blue R-250 in 50% methanol, destained, and the bands of interest excised and sequenced.

Figure 5:
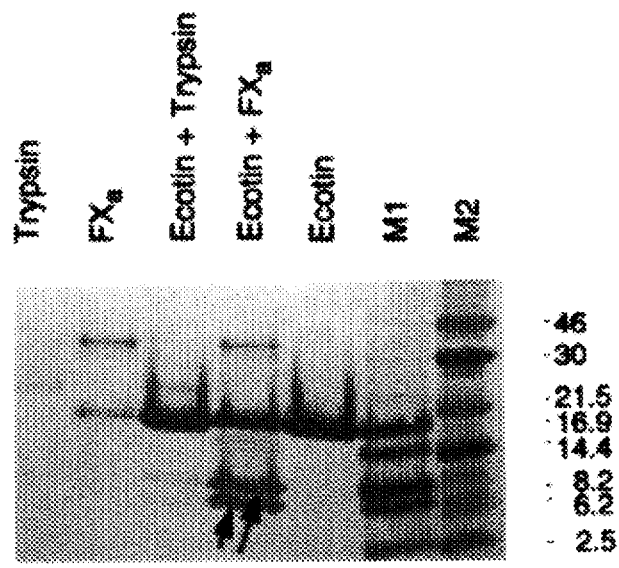
FIG. 5. Cleavage of ecotin by FXa and trypsin and reactive site determination. Samples were incubated as described in the text for 139 hours at room temperature, reduced, run on 16% Tricine gels and blotted onto PVDF. Lane 1, trypsin. Lane 2, FXa. Lanes 3 and 4, ecotin with trypsin and FXa, respectively. Lane 5, ecotin. Lanes 6 and 7, molecular weight markers from LKB and Amersham, respectively, with the associated Mr values ×10$^{-3}$. The amino terminal sequence of the lower band in Lane 4 (~6.2 kDa) was (SEQ ID NO:7) the amino terminal sequence of the upper band in Lane 4 (~8.2 kDa) was (SEQ ID NO:8) and corresponded to the amino terminus of ecotin.

The interaction of ecotin with FXa results in a slow cleavage of the inhibitor by the enzyme under certain in vitro conditions. FIG. 5 illustrates the amount of cleavage of ecotin by trypsin and by FXa at pH 4.0 in 139 hours. The inhibitor appears to be less sensitive to cleavage by trypsin than by FXa under these conditions. The same experiment conducted at pH 7.5 showed a similar relationship between trypsin and FXa cleavage, although the total amount of cleavage occurring at neutral pH was much less than that occurring at pH 4.0, where hydrolysis is favored (data not shown). Arrows indicate the bands which were later excised from the blot and sequenced. The N-terminal sequences obtained (FIG. 5) revealed that FXa cleaves ecotin between M84 and M85.

Molecular Weight Determination of Ecotin•FXa Complex

Size exclusion chromatography was performed with 2 TSK G3000SW-XL columns linked in series using HPLC and monitored at 214 nm. The columns were equilibrated and run at a flow rate of 0.5 ml/min in 50 mM Bis-Tris, 0.5M NaCl, pH 6.5. The molecular weight standards ($M_r$) used to calibrate the columns were sweet potato β-amylase (200,000), bovine gamma globulin (158,000), bovine serum albumin (68,000), human FXa (46,000) chicken ovalbumin (44,000), ecotin dimer (32,200; see below), human gamma interferon dimer (29,000), equine myoglobin (17,000), cytochrome C (12,500). The standards were purchased from Sigma, Boehringer Mannheim, and BioRad; gamma interferon was from Genentech. Ecotin was loaded at 140 μM. Ecotin and FXa (10 μM each) were incubated in TNCT buffer for 10 min at room temperature prior to injection. The molecular weight of the ecotin•FXa complex was calculated from linear regression analysis of a plot of the log molecular weight versus ratio of elution volume to void volume (Ve/Vo). The molecular weight of the ecotin•FXa complex, determined from a plot of log molecular weight versus Ve/Vo (FIG. 6), was 139,000 and suggests that the complex consists of 1 mole of ecotin dimer (see below) and 2 moles of FXa; (ecotin)$_2$•(FXa)$_2$ has a calculated molecular weight of 124,200. FXa eluted near its molecular weight of 46,000, whereas ecotin eluted as a dimer with a molecular weight of 32,200; ecotin monomer has a calculated weight of 16,099.

Determination of Ecotin Dimer Dissociation Constant by Fluorescence Titration

The change in fluorescence of ecotin with concentration was carried out on an SLM Model 8000 spectrofluorimeter with excitation at 280 nm and emission at 340 nm. Ecotin (10 μM) and L-tryptophan (40 μM) were each consecutively diluted 2-fold in 50 mM Tris, pH 7.5, 150 mM NaCl, 2 mM CaCl$_2$ buffer. The ratio of the ecotin fluorescence to the L-tryptophan fluorescence was used to determine the dissociation constant for ecotin dimerization.

Figure 7:
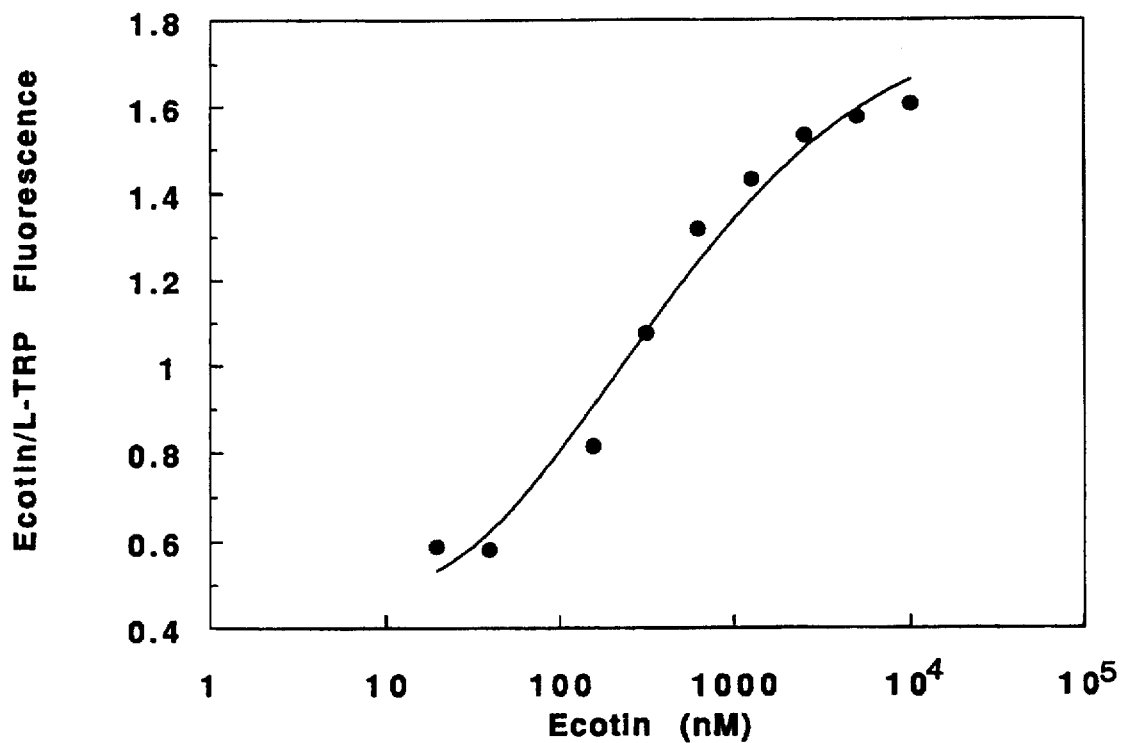
FIG. 7. Fluorescence titration of ecotin. The ratio of ecotin fluorescence to that of tryptophan fluorescence is plotted versus ecotin concentration. Excitation was at 280 nm and emission was at 340 nm. The curve represents a nonlinear regression analysis of the data to equation 9.

The dimerization of ecotin, which contains two tryptophans, was followed by measuring the change in fluorescence upon dilution compared to that of L-tryptophan. A sigmoidal dependence for the ratio of the ecotin/L-tryptophan fluorescence versus concentration was observed which is consistent with a two state model (FIG. 7). For the case of ecotin monomer (I) in equilibrium with dimer (I$_2$), I+I⇌I$_2$ with the equilibrium constant $K_d=[I]^2/[I_2]$ The total concentration of ecotin ([I$_T$]) is defined as [I$_T$]= [I]+2[I$_2$]. Combining these two equations and dividing by I$_T$ results in equation 7:

$$\text{Fraction monomer}=[I]/[I_T]=\{-K_d+(K_d^2+8 \cdot K_d \cdot [I_T])^{1/2}\}/4 \cdot [I_T] \quad (7)$$

Since $$[I]/[I_T]=1-(Fl_X-Fl_M)/(Fl_D-Fl_M) \quad (8)$$

where Fl$_M$ and Fl$_D$ are the relative fluorescence (ecotin fluorescence/L-tryptophan fluorescence) of ecotin monomer and dimer, respectively, and Fl$_X$ is the observed relative fluorescence. Combining equations 7 and 8 results in equation 9:

$$Fl_X=Fl_M+(Fl_D-Fl_M)\{-K_d+(K_d^2+8 \cdot K_d \cdot [I_T])^{1/2}\}/4 \cdot [I_T] \quad (9)$$

A nonlinear fit of the data to equation 9 results in a calculated K$_d$ value for ecotin dimerization of 390±150 nM.

Coagulation Assays and Prolongation of Clotting Times

Clotting times were performed using the ACL 300 Research Coagulation Analyzer. For the prothrombin time (PT) assays, the incubation time was set at 120 sec and acquisition time at 120 to 600 sec depending on the expected outcome of the assay. Membranes from 293 cells expressing TF (Paborsky, L. R. et al., Biochemistry 28:8072–8077 [1989]) were premixed with CaCl$_2$. The sample (plasma and inhibitor) and reagent (CaCl$_2$/TF) were automatically mixed together after a 2 min incubation at 37° C. The clotting time was determined by optical assessment. The total incubation time of inhibitor with plasma before addition of CaCl$_2$/TF was ~5 min. Final concentrations were 78 nM to 7.8 μM ecotin, 3.7 nM TF (0.9 μg/ml by protein content), 22.5 mM CaCl$_2$, and 50% plasma in a total volume of 160 μl.

For the activated partial thromboplastin time (APTT) assays, the activation time was set at 120 sec and acquisition time at 300 to 600 sec depending on the expected outcome of the assay. Citrated normal human plasma and inhibitor were incubated together. The sample (plasma and inhibitor) and activator (Instrumentation Laboratories Ellagic acid/ Phospholipid mix Test Reagent) were automatically pipetted and incubated together for 2 min at 37° C., then CaCl$_2$ was added and clotting time determined by means of optical assessment. The total incubation time of inhibitor with plasma was ca. 3 min before addition of activator, and 5 min before addition of CaCl$_2$. Final concentrations were 0.57 nM to 5.7 µM ecotin, 15.3 ug protein/ml 293 cell membranes, 8.3 uM ellagic acid, 8.3 mM CaCl$_2$, and 33.3% plasma in a total volume of 162 µl.

Figure 8:
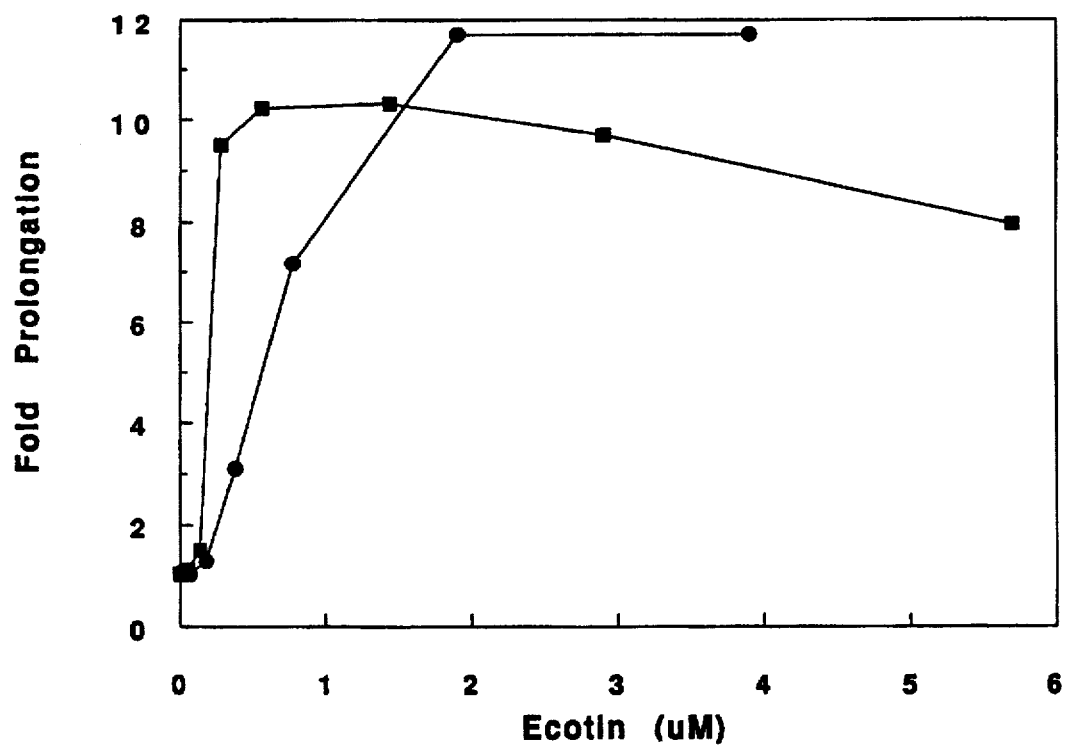
FIG. 8. Prolongation of clotting time in normal human plasma. The fold prolongation in clotting time is shown upon initiation by TF in the PT assay (●) or ellagic acid in the APTT assay (■). The uninhibited clotting times were 48 sec and 31 sec for the PT and APTT, respectively.

Wild type ecotin caused a 10-fold prolongation of clotting times at concentrations of ~0.3 µM and ~2 µM in APTT and PT assays, respectively (FIG. 8). The dose-response curve for the the APTT assay was particularly steep, with clotting times increasing from 1.5-fold to ~10-fold prolongation over a range of only 0.2 to 0.3 µM. The dose-response curve for the the PT assay was considerably less steep, requiring a concentration range of 0.2 to 2 µM for the same effect in prolongation of clotting time.

Results

The cloning, expression, and purification of ecotin show that ecotin is a potent anticoagulant and the most potent reversible FXa inhibitor characterized to date. Ecotin inhibits FXa with an equilibrium dissociation constant ($K_i$) of 17 pM. In addition, ecotin potently inhibits FXIIa, plasma kallikrein, and HLE with equilibrium dissociation constants of 25 pM, 41 pM, and 33 pM, respectively. These were determined using methods described for tight-binding inhibitors due to the high affinity with which ecotin binds these proteases (Morrison, J. F., supra; Bieth, J., supra). The reversible inhibition of ecotin (I) with these enzymes (E) is shown in Scheme A, a scheme from which equation (1) has been derived.

Scheme A

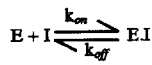

The association of ecotin with FXa is rapid with an association rate constant ($k_{on}$) of $1.35 \times 10^6 M^{-1} s^{-1}$. Because the affinity of ecotin for FXa is so high, dissociation of the ecotin•FXa complex was determined in the presence of excess HLE, which also binds ecotin with high affinity (supra). Thus, HLE trapped dissociated free ecotin and prevented reassociation with FXa. This method was used to determine the dissociation rate constant ($k_{off}$) of $6.5 \times 10^{-5} s^{-1}$ since direct measurement of $k_{off}$ in the absence of HIE resulted in too little free FXa to be measured accurately. This data also provided further confirmation of the observed equilibrium dissociation constant ($K_i$); the value obtained for $K_i$ determined by $k_{off}/k_{on}$ is 48 pM, which is only 3-fold higher than that measured under equilibrium conditions.

Based on active site titration, the inhibition of these enzymes by ecotin at high concentrations (>100•$K_i$) indicated that the E•I complexes formed were stoichiometric, i.e. 1:1 molar ratios of protease to ecotin were found. The methods used to calculate the equilibrium and kinetic constants assumed that these complexes contained one molecule each of ecotin and protease (Scheme A). The interaction of ecotin with FXa at high concentrations (10 µM range) was shown by gel filtration chromatography to elute with a molecular weight corresponding to a tetrameric complex consisting of two molecules of ecotin and two molecules of FXa (FIG. 5). Ecotin has previously been observed to form a complex with trypsin with similar stoichiometry (Chung, C. H. et al., supra). A mechanism for this complex formation is presented in Scheme B.

Scheme B

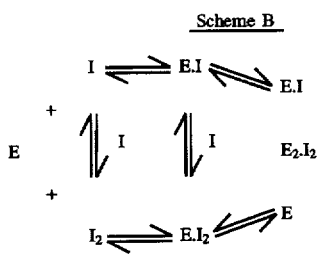

Figure 6:
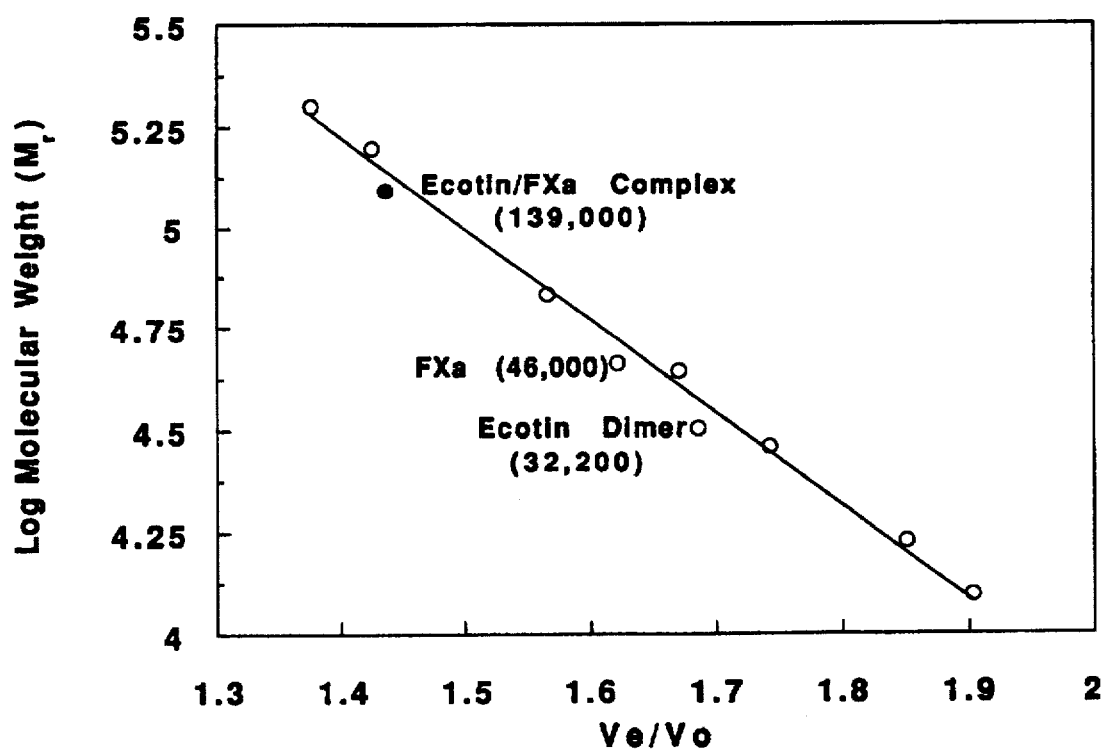
FIG. 6. Determination of the molecular weight of the ecotin •FX$_a$ complex by gel filtration. The ratio of elution volume/void volume (Ve/Vo) is plotted versus log molecular weight for the ecotin•FXa complex (●) and molecular weight standards (o). The line represents a least squares fit to the data. The ecotin. •FXa complex is plotted according to the calculated molecular weight of 124,200 for the (ecotin)$_2$•(FXa)$_2$ complex. Selected molecular weights are noted in parenthesis.

Scheme B is supported by gel filtration chromatography data (FIG. 5) which show that ecotin forms a dimer at a concentration of 140 µM; no evidence for dimer formation of FXa alone has been observed. The tetrameric complex that we observed at high concentrations likely results from the sequential addition of two FXa molecules to the ecotin dimer. This scheme is further supported based on evidence from ecotin fluorescence data (FIG. 6). Ecotin contains two tryptophans, at least one of which undergoes a fluorescence intensity change upon dilution. Fitting the data to a two state monomer/dimer model (2I ⇌ I$_2$) results in a $K_d$ value for ecotin dimerization of ca. 390 nM. This value is important for several reasons. It supports the observation that two molecules of FXa bind to the ecotin dimer since these experiments were carried out at concentrations above the $K_d$ for ecotin dimerization (FIG. 5). Furthermore, since equilibrium and kinetic measurements were conducted at a concentration range well below the $K_d$ for ecotin dimerization, the assumptions used in Scheme A and equation (1) to calculate these values are valid. Although we have not measured the affinity of the ecotin•FXa complex to either ecotin or another ecotin•FXa complex, it is reasonable to assume that the $K_d$ will be similar to that observed for ecotin dimerization.

The interaction of ecotin with FXa at pH 4 results in a slow cleavage of the inhibitor between M84 and M85. This occurs more rapidly with FXa than with trypsin (FIG. 4); very little cleavage was observed with either enzyme at pH 7.5. These results concur with earlier data which demonstrated that M84 is the $P_1$ reactive site for ecotin with trypsin, chymotrypsin, and porcine pancreatic elastase (McGrath, M. E. et al., *J. Biol. Chem*, supra). The observation that the inhibitor is cleaved does not mean that it no longer inhibits the enzyme; in fact, it is often found that the cleaved inhibitor is as potent as is the native inhibitor (Laskowski, M., Jr., & Kato, I., *Annu. Rev. Biochem.* 49:593–626 [1980]).

Factor Xa is a trypsin-like serine protease whose substrates, including prothrombin and chromogenic peptides (Lottenberg, R. et al., *Methods Enzymol.* 80:341–361 [1981]), and whose inhibitors, including ATIII (Björk, I. & Danielsson, Å, supra), TFPI (Broze Jr., G. J. et al., *Biochemistry*, supra), antistasin (Dunwiddie, C. T. et al., supra), and most likely TAP (Dunwiddie, C. T. et al., *Biochemistry* 31:12126–12131 [1992]) possess an Arg in the $P_1$ position. We therefore made and tested a number of mutations at the ecotin $P_1$ residue to see what effect they would have on FXa binding affinity as well as any specificity changes towards other serine proteases. Of the five ecotin mutants which were constructed, two (M84R and M84K) were found to be slightly more potent than the wild type inhibitor in terms of inhibiting FXa (Table I). Surprisingly, even when the $P_1$ residue was changed to Asp or Glu, significant inhibition of FXa activity was observed, suggesting that residues other than $P_1$ make significant contributions to binding.

It is anticipated that ecotin could be covalently crosslinked as well. This could be either via a homofunctional or heterofunctional crosslinking agent commonly employed to those skilled in the art. Alternatively, a cysteine could be introduced through mutagenesis of the ecotin gene to form an ecotin homolog, which could subsequently be oxidized to form a disulfide linkage, resulting in an ecotin or ecotin homolog dimer. In addition, a gene fusion consisting of two tandem copies of the ecotin or ecotin homolog gene may be used. The ecotin monomers to make the dimer may be the same or different homologs of ecotin. A crosslinked ecotin or ecotin homolog dimer may have improved properties over the monomer with respect to potency, half-life, immunogenicity, or other properties.

The substitution of either Arg or Lys for the $P_1$ Met residue resulted in an overall decrease in specificity as evidenced by more significant inhibition of thrombin, Factor XIa, plasmin, and to a lesser extent, activated protein C (Table II). As expected, the M84R and M84K mutants no longer inhibited HLE (Table II). Thus, the net effect was to increase specificity for FXa over HLE, but decrease specificity for FXa relative to most of the plasma proteases tested. A similar phenomenon has been observed with α1-proteinase inhibitor, a serpin containing a Met in the $P_1$ position, which potently inhibits trypsin, HLE, and chymotrypsin. α1-Proteinase inhibitor (Pittsburgh), a naturally occuring mutant which has Arg in the $P_1$ position instead of Met, displays 10,000-fold decreased inhibition towards HLE, but is a more potent inhibitor of trypsin and the trypsin-like serine proteases thrombin, plasmin, FXa, Factor XIa, kallikrein, Factor XIIa, urokinase, and activated protein C (Travis, J. et al., supra; Scott, C. F. et al., supra; Patston, P. A. et al., supra; Heeb, M. J. et al., *J. Biol. Chem.* 265:2365-2369 [1990]). In addition, both the Kunitz inhibitor BPTI and the Kazal inhibitor from turkey ovomucoid third domain show potent inhibition of HLE when $P_1$ is Met which is greatly diminshed when $P_1$ is Lys; the converse is found for trypsin (Beckmann, J. et al., *J. Prof. Chem.* 8:101-113 [1989]; Bigler, T. L. et al., *Prof. Sci.* 2:786-799 [1993]). No inhibition was observed with ecotin or the $P_1$ mutants and TF/FVIIa or single chain t-PA, suggesting that the active sites of these proteases differ significantly from the others or that a region distal from the active site on the proteases prevents ecotin binding.

Thrombosis is a complex process involving coagulation, fibrinolysis, platelet adhesion and aggregation, and interactions of the endothelium (Badimon, L. et al., *Trends Cardiovasc. Med.* 1:261-267 [1991]). Thrombin plays a central role in this process since it cleaves fibrinogen to fibrin, activates platelets, and interacts with the vessel wall. The regulation of thrombosis using thrombin inhibitors has been extensively studied, however an alternative and potentially better strategy is the inhibition of FXa to prevent thrombin formation. The anticoagulant potential of both synthetic and recombinant inhibitors of FXa and thrombin have been evaluated in various clotting assays (Hauptmann, J. & Kaiser, B., *Blood Coag. Fibrinol.* 4:577-582 1993). Recent evidence has shown that FXa inhibitors increase t-PA induced thrombolysis and prevent reocclusion in a canine model of arterial thrombosis (Mellott, M. J. et al., *Fibrinolysis* 7:195-202 [1993]) and prevent venous thrombosis in a rabbit model (Vlasuk, G. P. et al., supra). Furthermore, FXa has been implicated in determining the procoagulant activity of whole-blood clots (Eisenberg, P. R. et al., *J. Clin. Invest.* 91:1877-1883 [1993]). Therefore, the inhibition of FXa by agents such as ecotin represents an attractive approach for clinical intervention in various thrombotic disorders.

At functionally useful concentrations based on in vitro clotting assays (ca. 500 nM), the interaction of ecotin with FXa is essentially irreversible since this concentration is so much larger than the $K_i$ (Bieth, J., *Biochem. Med.* 32:387-397 [1984]). Based on the kinetic parameters of ecotin with FXa and a maximum possible FXa concentration in blood of ca. 200 nM, the time for complete inhibition of FXa is approximately 7.4 sec (Bieth, J., *Biochem. Med. supra*). In addition, the ecotin•FXa complex is relatively stable in vitro with a half-life of ca. 3 h. Obviously many biological and physiological factors can affect this inhibiton, however the high affinity, fast on rate, and slow off rate predict that ecotin can play a significant role in vivo.

The inhibition of the contact activation proteases plasma kallikrein and FXIIa may in part explain the potent anticoagulant effect observed in the APTT assay (FIG. 8), which measures intrinsic coagulation pathway activation. Surface activation of FXII to FXIIa leads to the formation of FXIa and kallikrein. FXIa activates FIX to IXa, which in the presence of FVIII leads to the formation of FXa and ultimately a fibrin clot. Kallikrein can further activate FXII to produce more FXIIa (Schmaier, A. H. et al., supra). Therefore a molecule showing coordinate inhibition of FXa, FXIIa, and kallikrein may be a more potent anticoagulant than one that only inhibits FXa alone. The PT results show the fold prolongation in clotting time due to initiation by tissue factor (the extrinsicpathway) which reflects only inhibition of FXa since ecotin does not inhibit TF•FVIIa activity. Furthermore kallikrein also activates plasminogen to plasmin, catalyzes the release of the potent vasodilator bradykinin from high molecular weight kininogen, has been implicated in neutrophil activation, and may regulate complement activation (Schmaier, A. H. et al., supra). Therefore FXIIa and kallikrein as well as inhibitors of these proteases such as ecotin may play important roles in the regulation of inflammation and fibrinolysis as well as coagulation. Major clinical manifestations of contact activation include sepsis, disseminated intravascular coagulation, and adult respiratory distress syndrome (Bone, R. C., supra).

The physiological role of ecotin remains unknown. However, since ecotin does not inhibit any known *E. coli* proteases, its location in the periplasm may indicate a role in protecting the cell against external proteases (Chung, C. H. et al., supra). The inhibition of the pancreatic enzymes which are present in the mammalian gastrointestinal tract supports this hypothesis. The potent inhibition by ecotin of FXa as well as plasma kallikrein and FXIIa was unexpected and is somewhat more difficult to rationalize. Since ecotin is not homologous to any other known protease inhibitors, the x-ray crystal structure (McGrath, M. E. et al., *J. Mol Biol.*, supra; Shin, D. H. et al., *J. Mol. Biol.* 229:1157-1158 [1993]) may provide a greater understanding of the nature of the ecotin active site(s), and the mechanism of inhibition for FXa and other serine proteases.

E. PHARMACEUTICAL COMPOSITIONS

Dosage formulations of the compounds of the present invention to be used for therapeutic applications must be sterile. Sterility is readily accomplished by filtration through sterile filtration membranes such as 0.2 μ membranes. Protein formulations ordinarily will be stored in lyophilized form or as an aqueous solution. The pH of the protein preparations typically will be between about 3 and 11, more preferably from about 5 to 9, and most preferably from about 7 to 8. The preferred route of administration is by hypodermic needle.

Therapeutic protein formulations are generally placed into a container having a sterile access port, for example, an intravenous solution bag or vial having a stopper pierceable by a hypodermic injection needle.

Therapeutically effective dosages may be determined by either in vitro (see assays above) or in vivo methods. Based upon such assay techniques, a therapeutically effective dosage range may be determined. The range of therapeutically effective dosages will naturally be affected by the the route of administration. For injection by hypodermic needle, it may be assumed that the dosage is delivered into the body's fluids. For other routes of administration, the adsorption efficiency must be individually determined for ecotin or ecotin homologs by methods well-known in pharmacology.

The range of therapeutic dosages may range from about 0.001 nM to about 1.0 mM, more preferably from about 0.1 nM to about 100 μM, and most preferably from about 1.0 nM to about 50 μM.

A typical formulation of ecotin or an ecotin homolog as a pharmaceutical composition contains from about 0.5 to 500 mg of a compound or mixture of compounds as either the free acid or base form or as a pharmaceutically acceptable salt. These compounds or mixtures are then compounded with a physiologically acceptable vehicle, carrier, excipient, binder, preservative, or stabilizer, etc., as called for by accepted pharmaceutical practice. The amount of active ingredient in these compositions is such that a suitable dosage in the range indicated is obtained.

Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the ends of the present invention.

EXAMPLES

Materials

Human Factor Xa, activated protein C, thrombin, Factor VIIa, and Factor XIa were purchased from Haematologic Technologies, Inc. Bovine trypsin, bovine chymotrypsin, Triton X-100, 4-methylumbelliferyl p-guanidinobenzoate (MUGB) and CHAPS were from Sigma. Human leukocyte elastase (HLE) was from Elastin Products, Inc. Human plasmin was purchased from Kabi. Human Factor XIIa and human plasma kallikrein were obtained from Enzyme Research Laboratories, Inc. Single chain tissue plasminogen activator (t-PA) was obtained from N. Paoni (Genentech). The substrates (supplier) are as follows: $N^\alpha$-Benzoyl-L-arginine-ρ-nitroanilide (BAPA) (Bachem); Spectrozyme fXa (American Diagnostica); S2366, S2302, and S2288 (Chromogenix); S2251 (Kabi); MeOSuc-Ala-Ala-Pro-Val-pNA (SEQ ID No. 9) (Calbiochem); Suc-Ala-Ala-Pro-Phe-pNA (SEQ ID No. 10) (Sigma). Recombinant human $TF_{1-243}$ was produced in *E. coli* and purified as previously described (Paborsky, L. R. et al., supra). Prepoured polyacrylamide gels were purchased from Novex; molecular weight standards were from Amersham (Rainbow) and LKB (horse myoglobin peptides). DEAE fast flow and Superdex resins were from Pharmacia LKB Biotechnology, Inc. Silica adsorbant support was purchased from Davison Chemicals. Oligonucleotides were synthesized using hydrogen phosphonate chemistry (Froehler, B.C. et al., *Nucleic Acids Res.* 14:5399–5407 [1986]) and purified by polyacrylamide gel electrophoresis (PAGE). *E. coli* strain XL1-Blue MRF' was purchased from Stratagene. Restriction enzymes were from New England Biolabs. Affigel-15 was obtained from Bio-Rad. All other reagents were obtained were of the highest grade commercially available.

Example 1

Cloning of the Ecotin Gene

All DNA manipulations were performed according to standard procedures unless otherwise indicated (Sambrook et al., supra). The ecotin gene was cloned from *E. coli* chromosomal DNA using the polymerase chain reaction (PCR). Based on the published sequence of the ecotin gene (McGrath, M. E. et al., *J. Biol. Chem*, supra; Lee, H. R. et al., supra), two primers were designed which were complementary to the 5' and 3' ends of the gene, and additionally encoded XbaI and BamHI restriction sites. The primers had the following sequences: 5'-CTGGACTCTAGAATTATGA AGACCATTCTACCTGCAGTA (SEQ ID No. 11) and 5'-TCTGAGGATCCAGGCCTTTAGCGAACTACCGCGT TGTCAAT (SEQ ID No. 12). The PCR reaction was carried out with Ampli-Taq polymerase on *E. coli* strain W3110 (ATCC 27325) chromosomal DNA using a Perkin-Elmer thermocycler under the following conditions: denaturation 1 min at 94° C., annealing 2 min at 50° C., and extension 3 min at 72° C. After 30 cycles the reaction was phenol/chloroform extracted, ethanol precipitated, and digested with XbaI and BamHI. The digest was then electrophoresed on a 5% polyacrylamide gel in 89 mM Tris-borate, 1 mM EDTA, pH 7.9; the gel was stained with ethidium bromide, and a band of approximately 500 base pairs was excised and eluted. The ecotin expression vector pEt3 was created by ligating the fragment obtained from the PCR reaction into a derivative of phGH1 (Chang, C. N. et al., Gene 55:189–196 [1987]) from which the XbaI-BamHI insert had been removed. After transformation of the ligation mixture into *E. coli* strain 27C7, a derivative of W3110, plasmid DNA from several ampicillin resistant colonies was subjected to restriction analysis and dideoxy sequencing (Sanger, F., Nicklen, S., and A. R. Coulsen, *Proc. Natl. Acad. Sci. USA* 74:5463–5467 [1977]). A plasmid which encoded the correct ecotin sequence, pEt3, was retransformed into *E. coli* strain 27C7, for expression.

Example 2

Expression and Purification of Recombinant Ecotin

Cultures of 27C7 pEt3 were grown at 37° C. for 30 hours in an aerated 10 liter fermentor in medium containing 110 ug/ml ampicillin, 11 g/l yeast extract, 11 g/l casein hydrolysate, 16.4 mM $K_2HPO_4$, 9.2 mM $NaH_2PO_4$, 47.4 mM $(NH_4)_2SO_4$, 3.7 mM sodium citrate, 22.1 mM KCl, 7.7 mM $MgSO_4$, 110 μM $FeCl_3$, 15 μM $ZnSO_4$, 16.2 μM $CoCl_2$, 15.9 μM $Na_2MoO_4$, 17.6 μM $CuSO_4$, 17.7 μM $H_3BO_3$, and 18.2 μM $MnSO_4$. Glucose was added to maintain glucose excess or avoid anaerobiosis, depending on cell density, and the pH was maintained at pH 7.4 with the addition of $NH_4OH$. The cell density at harvest was 116 $OD_{550}$.

Recombinant ecotin was purified as follows. Frozen cell paste (400 g) was subjected to osmotic shock by thawing in 10 volumes of 20 mM Tris, 5 mM EDTA, pH 7.5 and stirring at 4° C. for 15 min. The cells were removed by centrifugation at 10,800×g for 45 min, and the supernatant was clarified by filtration through a 0.45 micron membrane. The periplasmic fraction obtained (3000 ml) was mixed with 500 ml DEAE-Sepharose fast flow which had been previously equilibrated in 20 mM Tris, 5 mM EDTA, pH 7.5, and allowed to settle at 4° C. overnight. The supernatant containing the ecotin was then decanted and filtered through a 0.45 micron membrane. A portion of the supernatant (500 ml) was adjusted to 0.1M NaCl, and loaded onto 200 ml of silica adsorbant support in a XK50 Pharmacia column equilibrated in phosphate buffered saline (PBS) at pH 7.4. The column was washed with PBS and eluted with 7.5M urea, 50 mM Tris, 5 mM glycine, pH 8.5. A fraction of the silica column eluate was adjusted to pH 3.0 with HCl and loaded onto a Vydac C4 reverse phase HPLC column (10×250 mm) equilibrated with 0.1% TFA. The column was washed and then eluted with a linear gradient of 25 to 40% acetonitrile over 50 min. Following analysis by SDS PAGE, fractions containing ecotin were pooled and acetonitrile was evaporated under a stream of nitrogen. The resulting concentrated pool was subjected to size exclusion chromatography on a Superdex column (SX200, 26/60) equilibrated with 50 mM Tris, pH 7.5 at 6° C., at a flow rate of 2 ml/min. Fractions containing ecotin from several such runs were pooled and passed over a Pharmacia Q-Sepharose HR column (16×100 mm) equilibrated in 50 mM Tris, pH 8.0, to reduce endotoxin levels; purified ecotin was stored at −80° C.

Example 3

Ecotin Mutants

The phagemid used for mutagenesis was made by subcloning the 505 base pair XbaI/BamHI fragment of pEt3, which encodes the ecotin gene and its native signal sequence, into phagemid pA4G32. The pA4G32 phagemid was originally constructed by subcloning the synthetic gene encoding the APPI sequence (Castro, M. et al, *FEBS Letters* 267:207–212 [1990]) in place of the human growth hormone sequence in the phagemid phGHam-g3 (Lowman, H. B. et al. *Biochemistry* 30:10832–10838 [1991]). The pA4G32 phagemid also contains the alkaline phosphatase promoter, stII secretion signal (deleted in the ecotin subclone), the f1 and colE1 origins of replication, and the ampicillin resistance gene. Site directed mutagenesis at the $P_1$ position, which changed Met84 to Arg, Lys, Ala, Glu, or Asp, was accomplished using directed oligonucleotide mutagenesis as described by Kunkel (Kunkel, T. A. *Proc. Natl. Acad. Sci USA* 82:488–492 [1985]). Clones obtained following mutagenesis were analyzed by dideoxy sequence analysis (Sanger, F. et al., supra). Phagemids encoding the desired mutations were then transformed into *E. coli* strain 27C7 and checked for expression as follows. One liter cultures of each mutant were grown for 20 h at 37° C. in low phosphate minimal media (Chang, C. N. et al., supra) containing 50 ug/ml carbenicillin (no carbenicillin for 27C7 control). The cells were harvested by centrifugation and the periplasmic contents obtained by resuspending the pellets in 4 mM 10 mM Tris, pH 8.0, 1 mM EDTA, osmotically shocking the cells. After stirring for 1 h at 4° C., the suspension was spun and the supernatant harvested. These samples were assayed for ecotin expression by trypsin inhibition assays (data not shown) and by SDS-PAGE (FIG. 2).

Mutant ecotin proteins were purified from the shockates by binding to 2.5 ml Affigel-15-trypsin affinity columns previously prepared according to the manufacturer's directions. The columns were equilibrated and washed with 20 mM Tris, pH 7.5, 5 mM $CaCl_2$ and eluted with 10 mM HCl. Fractions containing inhibitory activity were pooled and further purified by reverse phase HPLC using a 10×250 mm 218TP510 Vydac C18 column (5 micron), Waters system (Model 510 pumps, 490E UV detector at 214 nm, and Waters Expert Ease version 3.0 Chromatography Software). After loading and washing in 0.1% TFA, a 15 to 60% gradient of $CH_3CN$ containing 0.1% TFA (0.5%/min, 5 ml/min, 1 min/fraction) was used to elute the column; the ecotin mutants eluted at ~40% $CH_3CN$. Active fractions were vacuum evaporated to remove the $CH_3CN$ and stored at 4° C.

All references cited herein are expressly incorporated by reference.

What is claimed is:

1. An isolated DNA molecule encoding a serine protease inhibitor which inhibits Factor Xa which inhibitor is represented by formula IV $$R^1 - Ser - Thr - P^1 - Met - Ala - Cys - R^2 \quad (SEQ\ ID\ NO:\ 4) \quad IV$$

where $P^1$ is selected from the group consisting of Arg, and Lys;

$R^1$ represents amino acid residues 1–81 of ecotin;

$R^2$ represents amino acid residues 88–142 of ecotin.

2. The DNA molecule of claim 1 further comprising an expression control sequence operably linked to the DNA molecule.

3. An expression vector comprising the DNA molecule of claim 2 wherein the control sequence is recognized by a host cell transformed with the vector.

4. The vector of claim 3 that is a plasmid.

5. A host cell transformed with the vector of claim 4.

6. A method for expressing a DNA molecule encoding a serine protease inhibitor in a host cell, comprising culturing the host cell of claim 5 under conditions suitable for expression of the inhibitor.

7. The method of claim 6 further comprising recovering the inhibitor from the culture medium.

8. An isolated DNA molecule encoding a serine protease inhibitor which inhibits human leukocyte elastase (HLE) which inhibitor is represented by formula IV $$R^1 - Ser - Thr - P^1 - Met - Ala - Cys - R^2 \quad (SEQ\ ID\ NO:\ 4)$$

where $P^1$ is selected from the group consisting of Leu, and Val;

$R^1$ represents amino acid residues 1–81 of ecotin;

$R^2$ represents amino acid residues 88–142 of ecotin.

9. An isolated DNA molecule encoding a serine protease inhibitor which inhibits Factor XIIa which inhibitor is represented by formula IV $$R^1 - Ser - Thr - P^1 - Met - Ala - Cys - R^2 \quad (SEQ\ ID\ NO:\ 4)$$

where $P^1$ is selected from the group consisting of Ala, Glu and Asp;

$R^1$ represents amino acid residues 1–81 of ecotin;

$R^2$ represents amino acid residues 88–142 of ecotin.

* * * * *